United States Patent
Worden et al.

(10) Patent No.: US 11,452,813 B2
(45) Date of Patent: Sep. 27, 2022

(54) TIME MANAGEMENT FOR TIME-DEPENDENT THERAPY MANAGEMENT SYSTEMS, METHODS, AND DEVICES

(71) Applicant: Bigfoot Biomedical, Inc., Milpitas, CA (US)

(72) Inventors: Alexander Howard Worden, Walnut Creek, CA (US); Kilty McGowan, Milpitas, CA (US); Pawel Drozdz, Milpitas, CA (US); Ross Naylor, Milpitas, CA (US); Kevin S. Lee, Milpitas, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 229 days.

(21) Appl. No.: 16/380,081

(22) Filed: Apr. 10, 2019

(65) Prior Publication Data
US 2019/0307957 A1    Oct. 10, 2019

Related U.S. Application Data

(60) Provisional application No. 62/655,420, filed on Apr. 10, 2018.

(51) Int. Cl.
*A61M 5/142* (2006.01)
*A61M 5/172* (2006.01)
*G06F 1/14* (2006.01)

(52) U.S. Cl.
CPC .......... *A61M 5/142* (2013.01); *A61M 5/1723* (2013.01); *G06F 1/14* (2013.01);
(Continued)

(58) Field of Classification Search
CPC .......... A61M 2005/14208; A61M 2205/3569; A61M 2205/52; A61M 2230/201;
(Continued)

(56) References Cited

U.S. PATENT DOCUMENTS

2004/0215272 A1* 10/2004 Haubrich ............... A61N 1/372
   607/27
2011/0009813 A1* 1/2011 Rankers ............. A61B 5/15087
   604/66
(Continued)

FOREIGN PATENT DOCUMENTS

EP    2186030    5/2010
EP    2186030 A2 * 5/2010 ............. G16H 40/67
(Continued)

OTHER PUBLICATIONS

PCT International Search Report and Written Opinion in International Appln. No. PCT/US2019/026716, 13 pages.

*Primary Examiner* — Nathan R Price
*Assistant Examiner* — Melissa A Snyder
(74) *Attorney, Agent, or Firm* — Brake Hughes Bellermann LLP

(57) ABSTRACT

A therapy delivery device stores a plurality of time-dependent therapy settings. The therapy delivery device is configured to administer time-dependent therapies according to the time-dependent therapy settings based on a universal conception of time that is independent of a local time zone. A mobile device includes a display adapted to depict information about therapy or therapy-related data as compared to a local time that is stored on the mobile device based on a local time zone setting found in the mobile device. The therapy delivery device and a mobile application executing on the mobile device are configured to keep separate clocks, (Continued)

with each clock being based on a universal concept of time that is independent of a local time zone.

18 Claims, 8 Drawing Sheets

(52) U.S. Cl.
CPC ............. *A61M 2005/14208* (2013.01); *A61M 2205/3553* (2013.01); *A61M 2205/3561* (2013.01); *A61M 2205/3569* (2013.01); *A61M 2205/3584* (2013.01); *A61M 2205/50* (2013.01); *A61M 2205/502* (2013.01); *A61M 2205/52* (2013.01); *A61M 2230/201* (2013.01)

(58) Field of Classification Search
CPC ........ A61M 5/1723; A61M 2205/3553; A61M 2205/3561; A61M 5/142; A61M 2205/3584; A61M 2205/50; A61M 2205/502; G06F 1/14
See application file for complete search history.

(56) References Cited

U.S. PATENT DOCUMENTS

| | | | |
|---|---|---|---|
| 2014/0321246 A1* | 10/2014 | Carlsgaard | A61B 5/14532 368/10 |
| 2016/0038675 A1* | 2/2016 | Estes | A61M 5/1723 604/506 |
| 2016/0287807 A1* | 10/2016 | Madsen | G01D 5/25 |
| 2017/0203039 A1 | 7/2017 | Desborough et al. | |

FOREIGN PATENT DOCUMENTS

| | | | | |
|---|---|---|---|---|
| EP | 2186030 B1 * | 2/2019 | | G16H 40/40 |
| WO | WO 2011/060923 | 5/2011 | | |
| WO | WO-2017013464 A1 * | 1/2017 | | G01R 33/0206 |

* cited by examiner

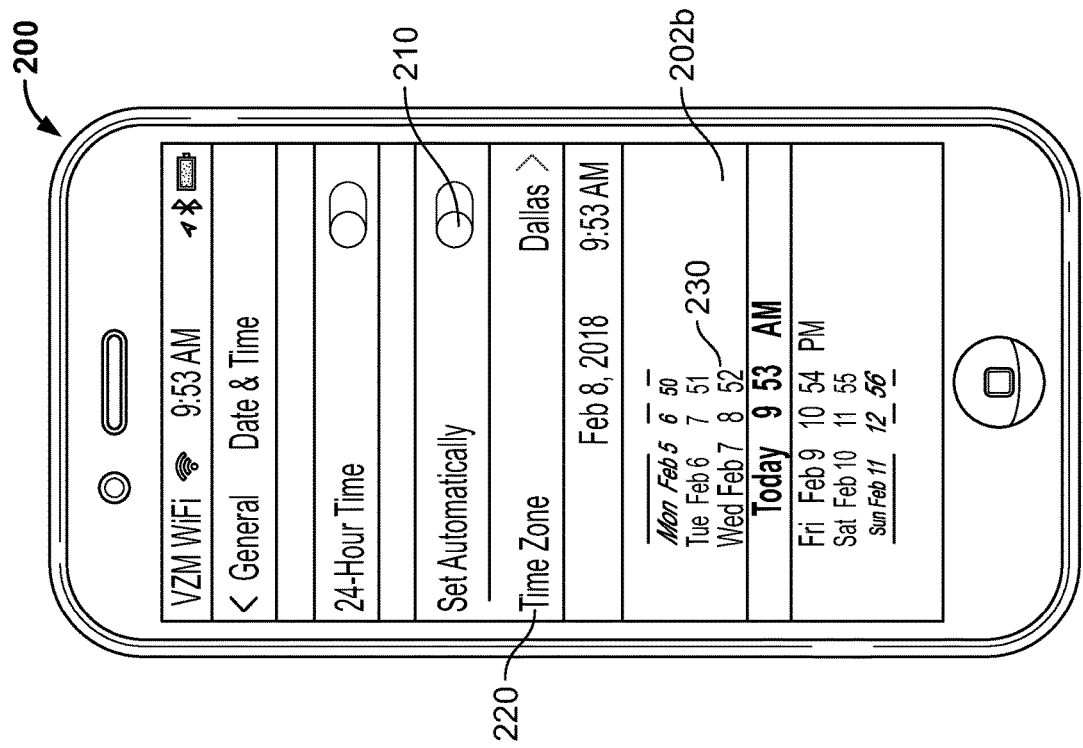
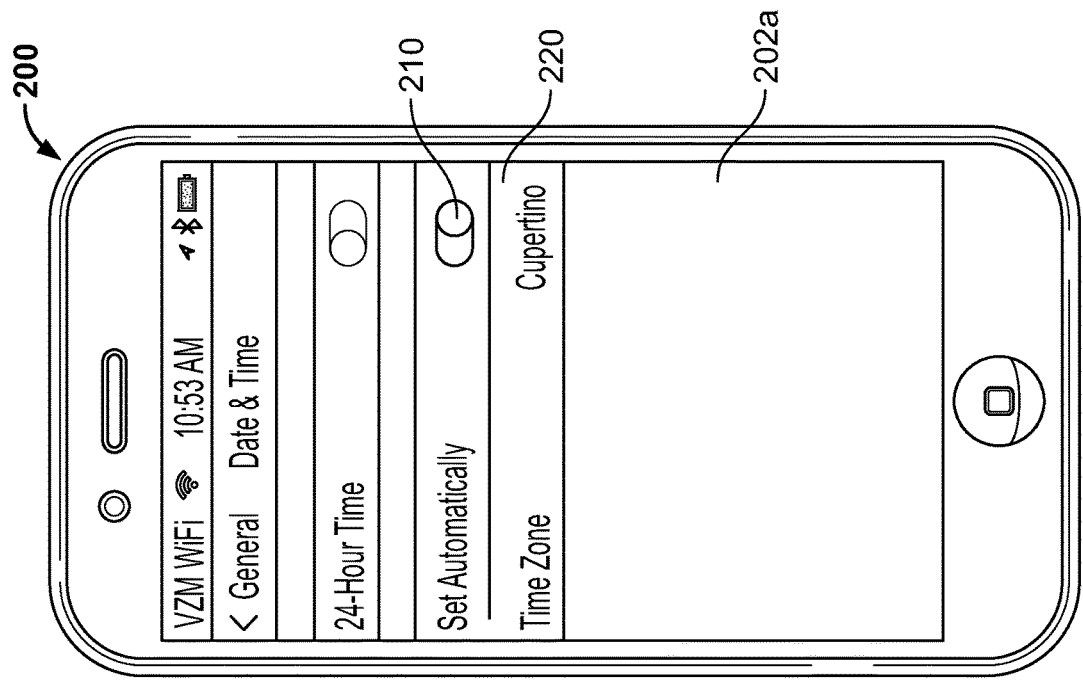
FIG. 2B (Prior Art)
FIG. 2A (Prior Art)

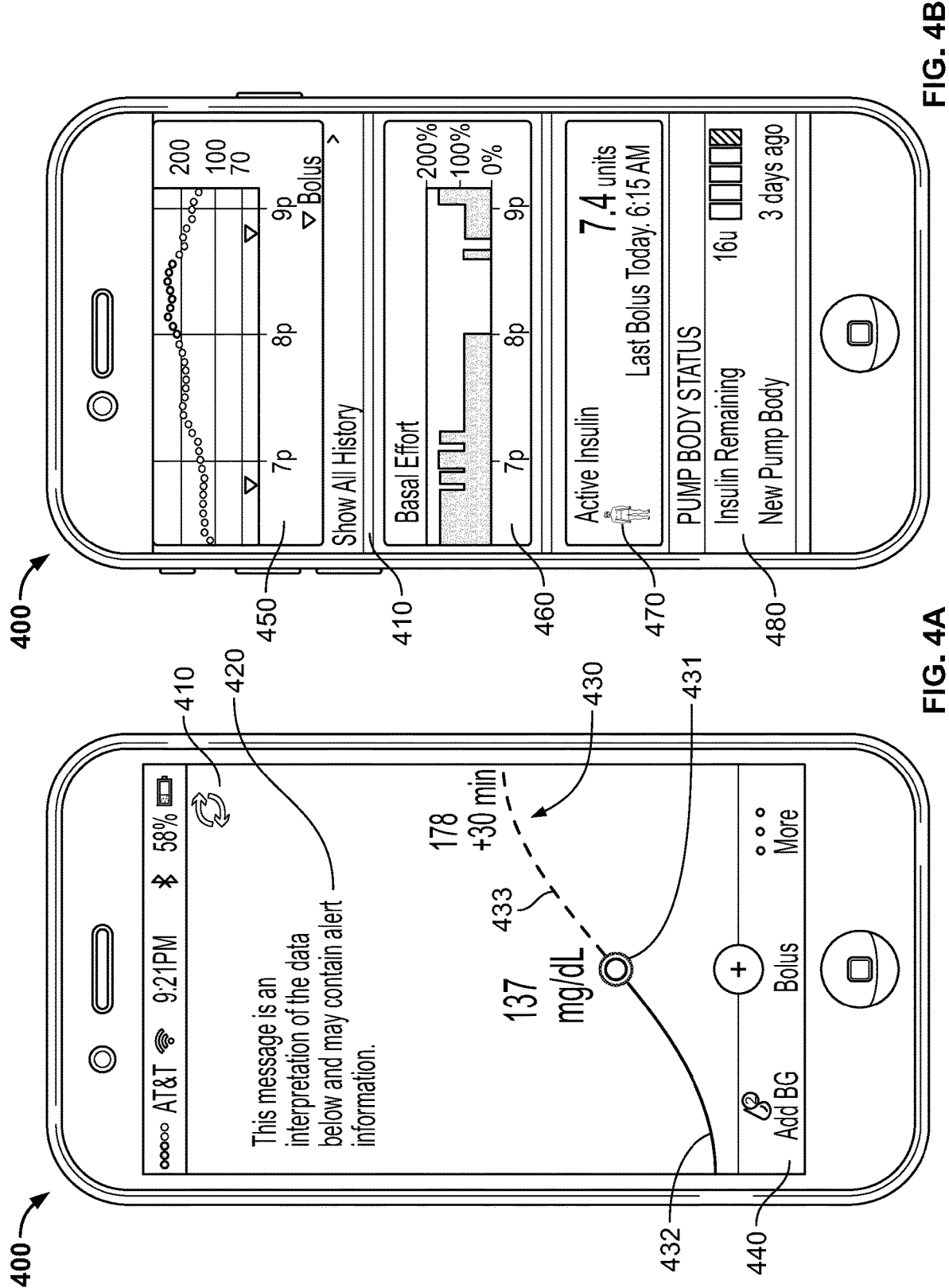

TIME MANAGEMENT FOR TIME-DEPENDENT THERAPY MANAGEMENT SYSTEMS, METHODS, AND DEVICES

CROSS-REFERENCE TO RELATED APPLICATION

This application claims priority to U.S. Application Ser. No. 62/655,420, filed on Apr. 10, 2018. The disclosure of the prior application is considered part of the disclosure of this application, and is incorporated in its entirety into this application.

TECHNICAL FIELD

This invention relates to the storage and communication of time in therapy management systems, methods, and devices that use time-dependent therapy settings.

BACKGROUND

Diabetes mellitus is a chronic metabolic disorder caused by an inability of a person's pancreas to produce sufficient amounts of the hormone insulin such that the person's metabolism is unable to provide for the proper absorption of sugar and starch. This failure leads to hyperglycemia, i.e. the presence of an excessive amount of glucose within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Self-monitoring of blood glucose and the self-administration of insulin is the typical method for treating diabetes. In order to assist with this self-treatment, many diabetes-related devices and systems (e.g., blood glucose meters, insulin pumps, etc.) can store time-dependent therapy settings (e.g., different basal insulin delivery rates depending on the time and/or day).

SUMMARY

Some embodiments of a time-dependent therapy management system can include a therapy delivery device and a mobile device in wireless communication with the therapy delivery device. The mobile device can be configured to display information regarding therapies administered by the therapy delivery device, future scheduled therapies to be administered by the therapy delivery device, and other information related a patient's medical treatment. A patient/user can also use the mobile device to change settings of the therapy delivery device and provide information to the therapy delivery device that is relevant to therapies administered by the therapy delivery device (e.g., information on meals consumed, exercise or other physical activities performed, information on medical treatments administered using other delivery devices, etc.).

The therapy delivery device can store a plurality of time-dependent therapy settings. The therapy delivery device can be configured to administer time-dependent therapies according to the time-dependent therapy settings based on a universal conception of time that is independent of a local time zone. The mobile device can include a display adapted to depict information about therapy or therapy-related data as compared to a local time that is stored on the mobile device based on a local time zone setting found in the mobile device. The therapy delivery device and the mobile device can therefore be configured to keep separate clocks, with a clock of the therapy delivery device being based on a universal concept of time that is independent of a local time zone (e.g., independent of a time zone setting of the mobile device), while the mobile device can maintain a clock that determines a time based on a local time zone and/or a time zone setting entered by a user of the mobile device. As such, the therapy delivery device can administer therapies to a patient based on the universal concept of time such that therapy administration is not affected by a time zone setting of the mobile device, or a change in time zone setting (e.g., due to the patient traveling from one time zone to another, or due to the patient manually changing a time zone setting of the mobile device) of the mobile device. Likewise, the mobile device maintains a clock that is based on a local time zone and/or time zone setting of the mobile device and can display information regarding therapies administered by the therapy delivery device, future scheduled therapies to be administered by the therapy delivery device, and other information related the patient's medical treatment based on the local time zone or time zone setting of the mobile device, thus allowing the patient or another user to view the information with time settings that are more relevant to the patient/user (e.g., because they are based on the current time zone of the user, rather than a time zone independent universal time).

Furthermore, one or both of the mobile device or the therapy delivery device can include software protocols for adjusting time related information from a time based on a local time zone and/or time zone setting of the mobile device to a time based on the universal conception of time that is independent of the local time zone and vise-versa. For example, the mobile device can include software that converts time stamps for time related information from a time based on a time zone setting of the mobile device to a time based on the universal conception of time that is independent of the local time zone prior to communicating the time stamps and time related information to the therapy delivery device. The software executing on the mobile device can also be configured to convert time stamps for information received from the therapy delivery device from times based on the universal conception of time that is independent of the local time zone to times that reflect a current time zone setting of the mobile device. Alternatively, or additionally, such time stamp conversions can be performed by software executing on the therapy delivery device.

In some cases, the mobile device can be a smartphone. In some cases, the information depicted on the mobile device can be information presented in a mobile application running on the smartphone. In some cases, the information depicted on the mobile device can include a graphical display of the therapy delivered and/or the therapy related data based on the local time. In some cases, the local time zone can be determined via a network or cloud connection of the mobile device to a remote server that determines the time zone for the location of the mobile device. In some cases, location information determined by or received at the mobile device can be used to determine the local time zone. For example, a GPS component of the mobile device can be used to determine a location of the mobile device and the mobile device can subsequently determine the time zone based on the location information. As another example, the location of the mobile device can be determined based on information associated with a wireless communications access point (e.g., a cell tower) in communication with the mobile device. For example, the location of the communications access point can be used as a rough approximation for the location of the mobile device and the mobile device or another computing system in communication with the mobile device can determine the time zone based on this location information. In some cases, a user may manually set a local time zone for the mobile device, which may be an override of a local time zone. In some cases, the universal conception of time can be established on the therapy delivery device based on a universal conception of time found on a remote server. In some cases, the universal conception of time on the therapy delivery device is reestablished in response to a previously identified universal concept of time being lost (e.g., power is interrupted from a clock in the therapy delivery device).

In some cases, a mobile application running on the mobile device wirelessly receives data from the therapy delivery device that is time stamped with the universal conception of time and presents the received data to the user based on a local time zone setting within the mobile device. In some cases, the mobile application can use a time counter on the mobile device to determine the time since the mobile application received the timestamped data. In some cases, systems and methods provided herein can reestablish the universal concept of time in the therapy delivery device (e.g., after a power failure) based on the time counter running on the mobile device and a timestamped data previously received by the mobile application. In some cases, systems and methods provided herein can reestablish the universal concept of time in the therapy delivery device (e.g., after a power failure) based on a universal concept of time found on a remote server. In some cases, a mobile application can determine the current universal concept of time from a wireless communication from the therapy delivery device. In some cases, a mobile application that is not in communication with the therapy delivery device may estimate the current universal concept of time on the therapy delivery device by receiving a universal concept of time from a remote server. In some cases, the universal concept of time is not reestablished on the therapy delivery device unless the universal concept of time is indeterminate (e.g., due to a loss of power to an internal clock).

In some cases, the time-dependent therapy management system can be a diabetes management system that includes a glucose sensor and/or an insulin delivery device. For example, the therapy delivery device can be an insulin delivery device such as an insulin pump or insulin pen. In some cases, the mobile device can depict past, current, and/or scheduled insulin delivery data based on the local time. In some cases, the mobile device can depict past, current, and/or predicted blood glucose data based on the local time. In some cases, the mobile device can include a graphical display that includes time-aligned or overlapping displays of blood glucose data and insulin delivery data. In some cases, the graphical display can indicate how the data relates a time relative to the current time (e.g., 5 minutes ago, 1 hour ago, etc.)

In general, in one aspect, a medication delivery system includes a medication delivery device adapted to dispense medication, the medication delivery device comprising memory to store a medication delivery schedule or time-dependent dosage parameters based on a universal concept of time that is independent of a time zone in which the medication delivery device is located, the medication delivery device being further adapted to record medication delivery information or user actions, the medication delivery information or user actions being stored along with timestamps based on the universal concept of time; and a remote computing device in communication with the medication delivery device, the remote computing device configured to receive the timestamped medication delivery information or user actions from the medication delivery device, and present a visual display of the medication delivery information or user actions along with times, wherein the displayed times are determined using the timestamps based on the universal concept of time adjusted based on the current time zone setting of the remote computing device.

In some implementations, the medication delivery system can include one or more of the following features. The medication delivery device can be configured to receive blood glucose level information from a blood glucose monitor and store the blood glucose level information along with timestamps based on the universal concept of time that is independent of the time zone in which the medication delivery device is located. The remote computing device can be further configured to receive the timestamped blood glucose level information from the medication delivery device, and present a visual display of the blood glucose level information along with times based on the universal concept of time at which the blood glucose levels were determined adjusted based on the current time zone setting of the remote computing device.

The remote computing device can be configured to display the medication delivery information and the blood glucose level information concurrently. The remote computing device can be configured to convert the timestamps for the timestamped medication delivery information from times based on the universal concept of time to times based on the current time zone setting of the remote computing device using a mobile application clock maintained by a mobile application executing on the remote computing device that is distinct from an operating system clock of the remote computing device. The mobile application clock can be configured to use information indicating a current time zone for the remote computing device to determine a current time for the current time zone of the remote computing device independent of time zone settings of the remote computing device. The mobile application clock can be configured to use information indicating a current time zone for the remote computing device to determine a current time for the current time zone of the remote computing device independent of manual time settings of the remote computing device.

The mobile application executing on the remote computing device can be configured to initialize the mobile application clock using a time based on the universal concept of time received from a server. The server can be a mobile application server for the mobile application. The mobile application executing on the remote computing device can be configured to initialize the mobile application clock using timestamped information received from the medication delivery device. The timestamps for the timestamped information received from the medication delivery device can be based on the universal concept of time.

The mobile application executing on the remote computing device can be configured to maintain a universal concept of time for the mobile application clock by monitoring an elapsed time since the remote computing device was started or an elapsed time since the mobile application was initialized and comparing the elapsed time associated with information from the medication delivery device that indicates the universal concept of time to the current amount of elapsed time. The medication delivery device can be configured to maintain a delivery device clock that maintains a current time based on the universal concept of time. The medication delivery device can be configured to initialize the delivery device clock using time information received from the remote computing device.

The medication delivery device can be a medication delivery pen and a cap affixed to the medication delivery pen. The cap can be a smart cap that includes the memory to store the medication delivery schedule or time-dependent dosage parameters. The medication delivery device can include a portable pump housing that receives a medication supply for dispensation to a user, the pump housing at least partially containing a pump drive system to dispense medication from the medication supply through a flow path to the user; and controller that communicates with the pump drive system to dispense the medication to the user based on the stored medication delivery schedule.

In general, in another aspect, a method of operating a medication delivery system can include maintaining, at a medication delivery device, a clock based on a universal concept of time that is independent of a time zone in which the medication delivery device is located; storing, by the medication delivery device and in a memory of the medication delivery device, a medication delivery schedule or time-dependent dosage parameters based on the universal concept of time that is independent of a time zone in which the medication delivery device is located; recording, by the medication delivery device, medication delivery information or user actions and timestamp information for the medication delivery information or user actions, wherein the timestamp information is based on the universal concept of time; transmitting, by the medication delivery device to a remote computing device, the timestamped medication delivery information or user actions; and presenting, by the remote computing device, a visual display of the medication delivery information or user actions along with times, wherein the displayed times are determined using the timestamps based on the universal concept of time adjusted based on the current time zone setting of the remote computing device.

The method of operating the medication delivery system can further include one or more of the following steps and/or features. The medication delivery device can receive blood glucose level information from a blood glucose monitor. The medication delivery device can store, in the memory of the medication delivery device, the blood glucose level information along with timestamps based on the universal concept of time that is independent of the time zone in which the medication delivery device is located. The medication delivery device can transmit to the remote computing device the timestamped blood glucose level information from the medication delivery device. The remote computing device can present a visual display of the blood glucose level information along with times based on the universal concept of time at which the blood glucose levels were determined adjusted based on the current time zone setting of the remote computing device.

The remote computing device can convert the timestamped medication delivery information from times based on the universal concept of time to times based on the current time zone setting of the remote computing device using a mobile application clock maintained by a mobile application executing on the remote computing device that is distinct from an operating system clock of the remote computing device. The mobile application clock can be configured to use information indicating a current time zone for the remote computing device to determine a current time for the current time zone of the remote computing device independent of time zone settings of the remote computing device. The mobile application clock can be configured to use information indicating a current time zone for the remote computing device to determine a current time for the current time zone of the remote computing device independent of manual time settings of the remote computing device.

The subject matter described in this specification can be implemented in particular embodiments and can result in one or more of the following advantages. Lifesaving medical therapies can be delivered according to a timed-schedule independent of a change in time zone and/or a change in time zone setting of a device used to control a therapy delivery device. Medical therapy information related to past, current, and/or scheduled medicine delivery or other therapy administration can be recorded according to a universal time that is independent of a current time zone or time zone setting for a computing device and presented to a user according to the current time zone or time zone setting. Medical therapy information related to past and/or current patient parameter reading (e.g., blood glucose levels of the patient) can be recorded according to a universal time that is independent of a current time zone or time zone setting for a computing device and presented to a user according to the current time zone or time zone setting. Current time settings for a therapy delivery device, mobile device, or other component of a time-dependent therapy management system can be re-established after a loss of power event, reboot event, or other event that causes a time setting to be lost. The current time setting can be based on a universal conception of time that is independent of a local time zone or based on a current time zone or current time zone setting. Medical therapy information related to past, current, and/or scheduled medicine delivery or other therapy administration can be presented to users of various different computing devices according to time zone settings specific to each computing device and/or according to time zone settings that are specific to other computing devices. Thus medical treatment and review of medical treatment information is improved.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 2A illustrates an exemplary user interface for manually setting a time and/or time zone setting for a mobile computing device.

FIG. 2B illustrates an exemplary user interface for manually setting a time and/or time zone setting for a mobile computing device.

FIG. 4A illustrates an exemplary user interface for viewing medical therapy related information related to medical therapy administered by a time-dependent therapy management system.

FIG. 4B illustrates an exemplary user interface for viewing medical therapy related information related to medical therapy administered by a time-dependent therapy management system and for adjusting settings of the time-dependent therapy management system.

Like reference numbers and designations in the various drawings indicate like elements.

DETAILED DESCRIPTION

Figure 1A:
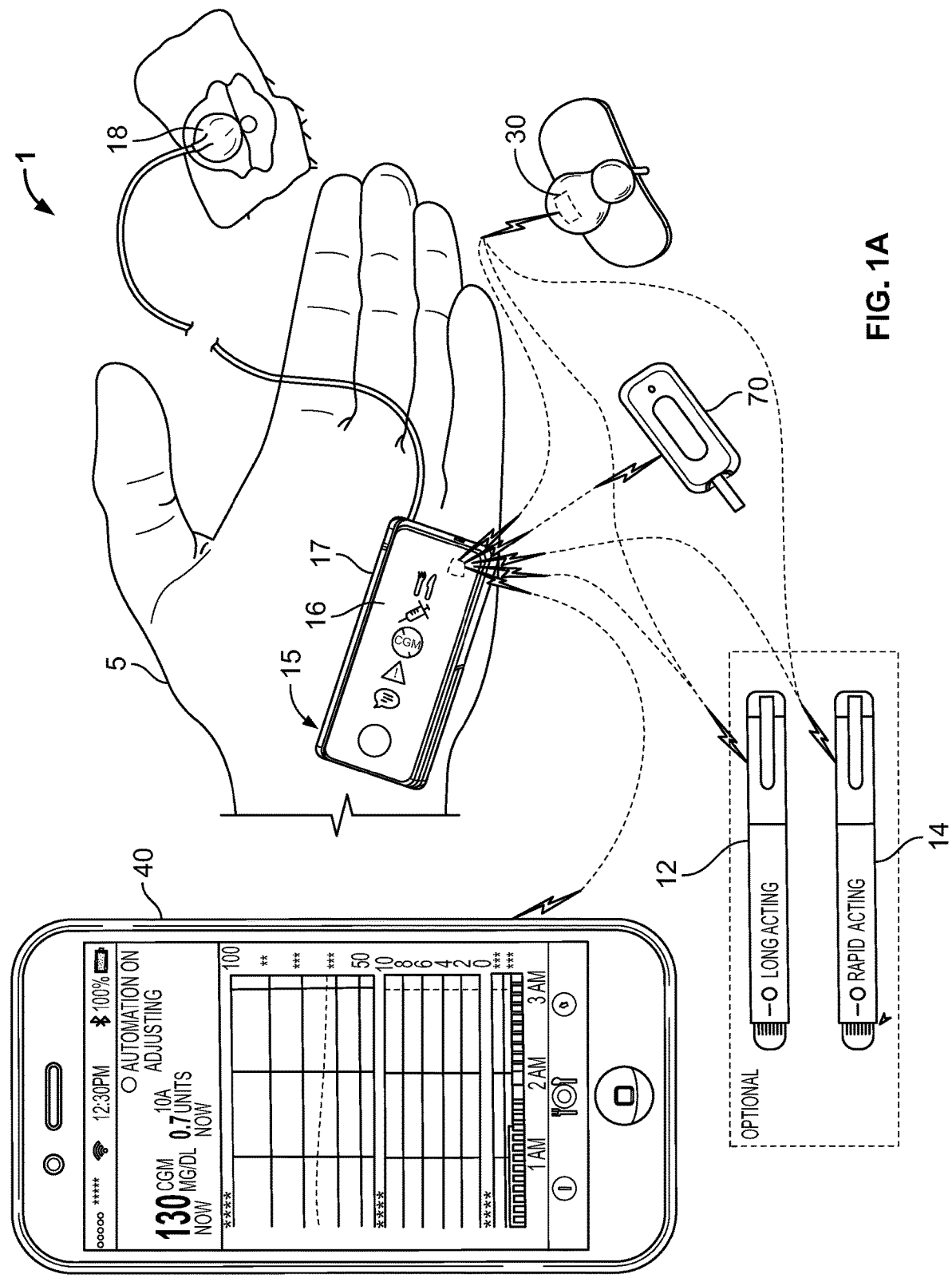
FIG. 1A illustrates an exemplary diabetes management system according to a first embodiment.

Therapy management methods, devices, and systems provided herein can record and/or schedule therapy related data or events or administered therapy based on a universal concept of time, such as a Universal Time Coordinated (UTC) clock, maintained by a therapy delivery device. The universal concept of time (e.g., the UTC clock) is independent of the current time zone of where the use is or where any component of the system is located. For example, the universal concept of time may be Greenwich Mean Time (GMT), Unix Time, or any other time standard that is not dependent on a particular time zone. Therapy management methods, devices and systems provided herein can present time to the user based on the designated time zone for the user or the location of devices or components of the system.

In some cases, therapy management methods, devices, and systems provided herein can use or include a remote computing device (e.g., a smartphone, tablet, PDA, personal computer, smart watch, etc.) that allows a user to view therapy related data, program or setup the system, deliver therapy, and/or conduct maintenance tasks. For example, in some cases the time displayed for a system that includes a remote mobile device (e.g., a smartphone) can display the time of therapy related data or events based on the universal concept of time corrected to be presented in a local time based on a time zone classification set in the remote mobile device.

Therapy management methods, devices, and systems can include a therapy schedule that is time-dependent. For example, medication delivery systems can include a time-dependent schedule for delivering the medication (e.g., via a medication delivery pump). In order to ensure that therapy is delivered according to the desired schedule, methods, systems, and devices provided herein rely on a trusted time source. In some cases, methods, devices, and systems provided herein can include a medication delivery pump configured to deliver medication at regular intervals (e.g., every 1 minute, every 5 minutes, every 10 minutes, every 15 minutes, every 20 minutes, every 30 minutes, or every hour). For example, methods, devices, and systems provided herein can be diabetes management systems that are, use, or include an insulin delivery pump. In some cases, insulin pump devices (or methods and systems including insulin pump devices) can include basal insulin delivery schedules that include different basal insulin delivery rates based on the time of day. For example, basal insulin delivery schedules can include different basal insulin delivery rates for different times of day based on a patient's typical or identified schedule of sleep/awake time and the patient's typical or identified schedule for meal and other food consumption. The time dependent insulin delivery schedule can also be based on other time of day and/or day of week factors, such as a patient's exercise schedule.

In some cases, diabetes management systems, methods, and devices provided herein can include or communicate with one or more glucose sensors (e.g., blood glucose meters, flash glucose monitors, continuous glucose monitors, etc.) and automate insulin delivery from the insulin delivery pump, which can be based in part on the time of the day. In some cases, methods, devices, and systems provided herein can include medication delivery devices that are manually operated by the user to deliver medication, but provide a medication delivery recommendation that is time dependent. In some cases, methods, devices, and systems provided herein can include or communicate with medication delivery pens adapted to be used by a user to inject medication. In some cases, methods, systems, and devices provided herein can include a pill container that recommends when to take a pill. In some cases, methods, devices, and systems provided herein can be diabetes management methods, devices, or systems that include insulin injection pens and can be adapted to provide a recommendation of an amount of insulin to inject based at least in part on the current time of the day. In some cases, methods, devices, and systems provided herein can be a cap for a medication delivery device or medication container (e.g., an insulin delivery pen, a syringe, a medicine bottle, etc.) that detects a time of removal of the cap from the medication delivery device or medication container and displays the time that the cap was removed from the medication delivery device or medication container.

In some cases, computing devices (e.g., smartphones, tablets, personal computers, etc.) can permit users to manually change the time or time zone classification. In some cases, such computing devices can be configured to automatically change the time of day and/or time zone based on a detected location of the computing device (e.g., using the detected cellular connection, using a global positioning system, etc.). In some cases, computing devices can permit a user to opt in or out of the automatic changing of time and/or the automatic setting of the time zone.

For example, FIGS. 2A and 2B depict the time and date setup screens 202a and 202b of an exemplary smartphone 200, which allow for a user to switch between the automatic setting of the time zone and clock using toggle switch 210. In FIG. 2A the automatic setting switch 210 is toggled to "on." As shown, the smartphone 200 automatically detects that the smartphone 200 is located in or within relative proximity to Cupertino, Calif., and thus sets "Cupertino" for the time zone field 220, thus the smartphone 200 uses the current local time for US Pacific time (the time zone in which Cupertino is located) and uses the Cupertino time zone. In FIG. 2B, the automatic setting switch 210 is toggled to "off," which allows the time zone field 220 to be set manually by a user of the smartphone 200 and for a time and date to be set manually using a scrolling menu 230. As shown in FIG. 2B, a user of the smartphone 200 can manually set the time zone as "Dallas," so that the smartphone 200 is set for US Central time (where Dallas, Tex. is located) and the scrolling menu 230 manual time setting can be set to any day and time desired by the user. A number of reasons may motivate a user to manually change a time zone setting or time setting of the smartphone 200. For example, a user may be traveling to locations having different time zones but may wish to have the smartphone 200 set to the user's home time zone such that the user is on the same time schedule as co-workers located in the user's home time zone. As another example, a user may be doing business or otherwise interacting with one or more persons or systems located in a different time zone (e.g., a stock trader located in the United States trading on the London stock exchange) and the user may find it easier to stay on schedule with respect to these interactions by manually changing time zone or time settings of the smartphone 200. As yet another example, a user may wish to manually adjust the time zone or time settings of the smartphone 200 to unlock time based features of an application (such as a game) or otherwise affect time based parameters of the application executing on the smartphone 200.

In systems, devices, and methods provided herein, the display of the system time can use the time zone (whether automatically or manually set) to adjust a universal concept of time, but ignore the specific time (whether automatically set or manually set) of a particular computing device (such as the smartphone 200). By using the time zone setting of the mobile device but ignoring the time setting in the computing device, methods, systems, and devices provided herein can display therapy relevant information according the user's actual or desired time zone. By ignoring the specific time being used by the computing device and instead using the therapy device's universal concept of time, methods, systems, and devices provided herein can ensure that therapy delivery or therapy recommendations are based on the time-dependent needs of a user rather than based on a potentially invalid time setting of the mobile device. For example, if the time set on the mobile device were to be considered the source of a true indication of the current time for a therapy delivery device that recommends or delivers therapy according to a time of the day, a user's manual change of the time could result in the unsafe delivery of medication or unsafe recommendations. For example, in some cases, users of mobile devices have been known to adjust the time setting of a mobile device forward in order to fool game apps running on the mobile device in order to give the user more game playing time, but such a change could result in the unsafe delivery of medication if the time on the mobile device were to be used to determine when to deliver medication.

Exemplary Medication Delivery Systems

FIG. 1A depicts an exemplary diabetes management system 1, in accordance with one or more embodiments of the present disclosure, including an insulin pump assembly 15 and a glucose sensor 30, which may be a continuous glucose monitor. As shown, the glucose sensor 30 is in wireless communication with insulin pump assembly 15. In some cases, a glucose sensor can be in wired communication with insulin pump assembly 15. In some cases, glucose sensor 30 can be a flash glucose monitor that is adapted to wirelessly transmit blood glucose values to insulin pump assembly 15 when it is interrogated by the insulin pump assembly 15. In some cases not shown, the glucose sensor can be incorporated into an insulin pump assembly. As shown, insulin pump assembly 15 can include a reusable pump controller 16 that forms part of the pump assembly. In some cases, reusable pump controller 16 is adapted to store a schedule of basal rates based on a time of the day. In some cases, reusable pump controller 16 is adapted to determine one or more basal delivery rates based on data from glucose sensor 30 in combination with a user-specific dosage parameters that are stored according to a time of the day. In some cases, glucose sensor 30 can act as a controller adapted to communicate basal delivery rates to insulin pump assembly 15 based on a schedule and/or based on current blood glucose data.

Insulin pump assembly 15, as shown, can include reusable pump controller 16 and a disposable pump 17, which can contain a reservoir for retaining insulin. A drive system for pushing insulin out of the reservoir can be included in either the disposable pump 17 or the reusable pump controller 16. In some embodiments, the drive system can be formed partially by the disposable pump 17 and partially by the reusable pump controller 16. Reusable pump controller 16 can include a wireless communication device, which can be adapted to communicate with a wireless communication chip in glucose sensor 30 and other diabetes devices in the system, such as those discussed below. For example, the reusable pump controller 16 can communicate with the glucose sensor 30 and other devices using near field communication (NFC), RF communication such as 433 RF radio communication, short distance communication (such as BLUETOOTH® based communication), WiFi, or any other suitable wireless or wired communication protocol.

In some cases, insulin pump assembly 15 can be sized to fit within a palm of a hand 5. Insulin pump assembly 15 can include an infusion set 18. Infusion set 18 can include a flexible tube that extends from the disposable pump 17 of the insulin pump assembly 15 to a subcutaneous cannula that may be retained by a skin adhesive patch (not shown) that secures the subcutaneous cannula to the infusion site. The skin adhesive patch can retain the cannula in fluid communication with the tissue or vasculature of the person with diabetes (PWD) so that the medicine dispensed through the tube passes through the cannula and into the PWD's body. A cap device can provide fluid communication between an output end of an insulin cartridge (not shown) and the tube of infusion set 18.

Glucose sensor 30 (e.g., a continuous glucose monitor) can include a housing, a wireless communication chip, and a sensor shaft. The wireless communication chip can be contained within the housing and the sensor shaft can extend outward from the housing. In use, the sensor shaft can penetrate the skin of a user to make measurements indicative of the PWD's blood glucose level or the like. In some cases, the sensor shaft can measure glucose or another analyte in interstitial fluid or in another fluid and correlate that to blood glucose levels. In response to the measurements made by the sensor shaft, the glucose sensor 30 can employ the wireless communication chip to transmit data to a corresponding wireless communication device housed in the pump assembly 15. Additionally or alternatively, the system 1 may include another glucose monitoring device that may utilize any of a variety of methods of obtaining information indicative of a PWD's blood glucose levels and transferring that information to reusable pump controller 16. For example, an alternative monitoring device may employ a micropore system in which a laser porator creates tiny holes in the uppermost layer of a PWD's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucosesensing contact lenses. Furthermore, it should be understood that in some alternative implementations, glucose sensor 30 can be in communication with reusable pump controller 16 and/or another computing device via a wired connection. In some cases, glucose sensor 30 can be adapted to provide blood glucose measurements for a PWD when in use for the PWD at regular or irregular time intervals. In some cases, glucose sensor 30 can detect and wirelessly transmit blood glucose measurements at least every thirty minutes, at least every fifteen minutes, at least every ten minutes, at least every five minutes, or at least every minute. In some cases, glucose sensor 30 can itself determine a basal delivery rate using methods provided herein and communicate that basal rate to the insulin pump assembly 15. In some cases, a mobile device 40 can receive glucose data from glucose sensor 30 (either through direct wired/wireless communication, or with the reusable pump controller 16 acting as a go-between for relaying blood glucose data from the glucose sensor 30, to the mobile device 40). The mobile device 40 can use the received blood glucose data to determine a basal delivery rate using methods provided herein and communicate the basal delivery rate to insulin pump assembly 15.

Diabetes management system 1 may optionally include a blood glucose meter 70 as an additional glucose sensor in addition to glucose sensor 30 (which may be a continuous glucose monitor or a flash glucose monitor). In some cases, blood glucose meter 70 can be in wireless communication with reusable pump controller 16 and/or mobile device 40. Blood glucose meter 70 can take a blood glucose measurement using one or more test strips (e.g., blood test strips). A test strip can be inserted into a strip reader portion of the blood glucose meter 70 and then receive the PWD's blood to determine a blood glucose level for the PWD. In some cases, blood glucose meter 70 is configured to analyze the characteristics of the PWD's blood and communicate (e.g., via a wired or wireless communication connection, such as NFC, RF, Short Range (e.g., BLUETOOTH®), WiFi, or other communication protocol) the information to reusable pump controller 16. In some cases, a user can manually input a glucose meter reading. Blood glucose meter 70 can be manually operated by a user and may include an output subsystem (e.g., display, speaker) that can provide the user with blood glucose readings that can be subsequently entered into the controller or user interface to collect the data from an unconnected BGM into the system. Blood glucose meter 70 may be configured to communicate data (e.g., blood glucose readings) obtained to reusable pump controller 16 and/or other devices, such as the mobile device 40 (e.g., a control device). Such communication can be over a wired and/or wireless connection, and the data can be used by system 1 for a number of functions (e.g., calibrating the glucose sensor 30, confirming a reading from the glucose sensor 30, determining a more accurate blood glucose reading for a bolus calculation, detecting a blood glucose level when the glucose sensor 30 is malfunctioning).

In some cases, the system 1 includes the mobile device 40 that can communicate with the reusable pump controller 16 through a wireless and/or wired connection with the reusable pump controller 16 (e.g. NFC, RF, Short Range (e.g., BLUETOOTH®), WiFi, or other communication protocol). In some cases, the mobile device 40 communicates wirelessly with one or more other diabetes devices of system 1. The mobile device 40 can be any of a variety of appropriate computing devices, such as a smartphone, a tablet computing device, a wearable computing device, a smartwatch, a fitness tracker, a laptop computer, a desktop computer, a PDA, a dedicated medical therapy system control device, and/or other appropriate computing devices. In some cases (for example, where the reusable pump controller 16 does not determine a basal delivery rate), the mobile device 40 can receive and log data from other elements of the system 1 and determine basal delivery rates using methods provided herein. In some cases, a user can input relevant data into the mobile device 40. In some cases, the mobile device 40 can be used to transfer data from the reusable pump controller 16 to another computing device (e.g., a back-end server, personal computer, or cloud-based device). In some cases, one or more methods provided herein can be performed or partially performed by the other computing device. In some cases, the mobile device 40 provides a user interface (e.g., graphical user interface (GUI), speech-based user interface, motion-controlled user interface) through which users can provide information to control operation of the reusable pump controller 16 and the system 1. For example, the mobile device 40 can be a mobile computing device running a mobile app that communicates with reusable pump controller 16 over short-range wireless connections as described above to provide status information for the system 1 and allow a user to control operation of the system 1 (e.g., toggle between delivery modes, adjust settings, log food intake and exercise, change a fear of hypoglycemia index (FHI), confirm/modify/cancel bolus dosages, and the like). For example, the mobile device 40 can be a commercial, off-the-shelf, computing device running a specialized application that provides the mobile device 40 with some or all of the specific functionality described herein. The specialized application can be, for example, an insulin delivery control application that can be used to change settings of one or more components of the system 1 (such as the insulin pump assembly 15) and display information related to medical treatments administered by the insulin pump assembly 15 and information collected by components of the system 1 such as the insulin pump assembly 15, the glucose sensor 30, and the blood glucose meter 70.

In some embodiments, system 1 may optionally include one or more manual injection devices 12 and 14 (e.g., syringes, insulin injection pens, a smart syringe with device communication capabilities, or the like) through which dosages of medication such as insulin (either or both long-acting insulin or rapid-acting insulin) or glucagon can be manually administered to a PWD. In some cases, a suggested dosage for a bolus to be administered using the manual injection devices 12 or 14 can be output to a user via the user interface of reusable pump controller 16, on a user-interface on the manual injection devices 12 or 14, on an accessory reversibly attachable to the manual injection devices 12 or 14, and/or the user interface of the mobile device 40. In some cases, the manual injection devices 12 or 14 can communicate through a wired and/or wireless connection with reusable pump controller 16 and/or the mobile device 40. In some cases, system 1 can allow users to input insulin deliveries made using a syringe or insulin pen.

Figures 1B, 1C, 1D:
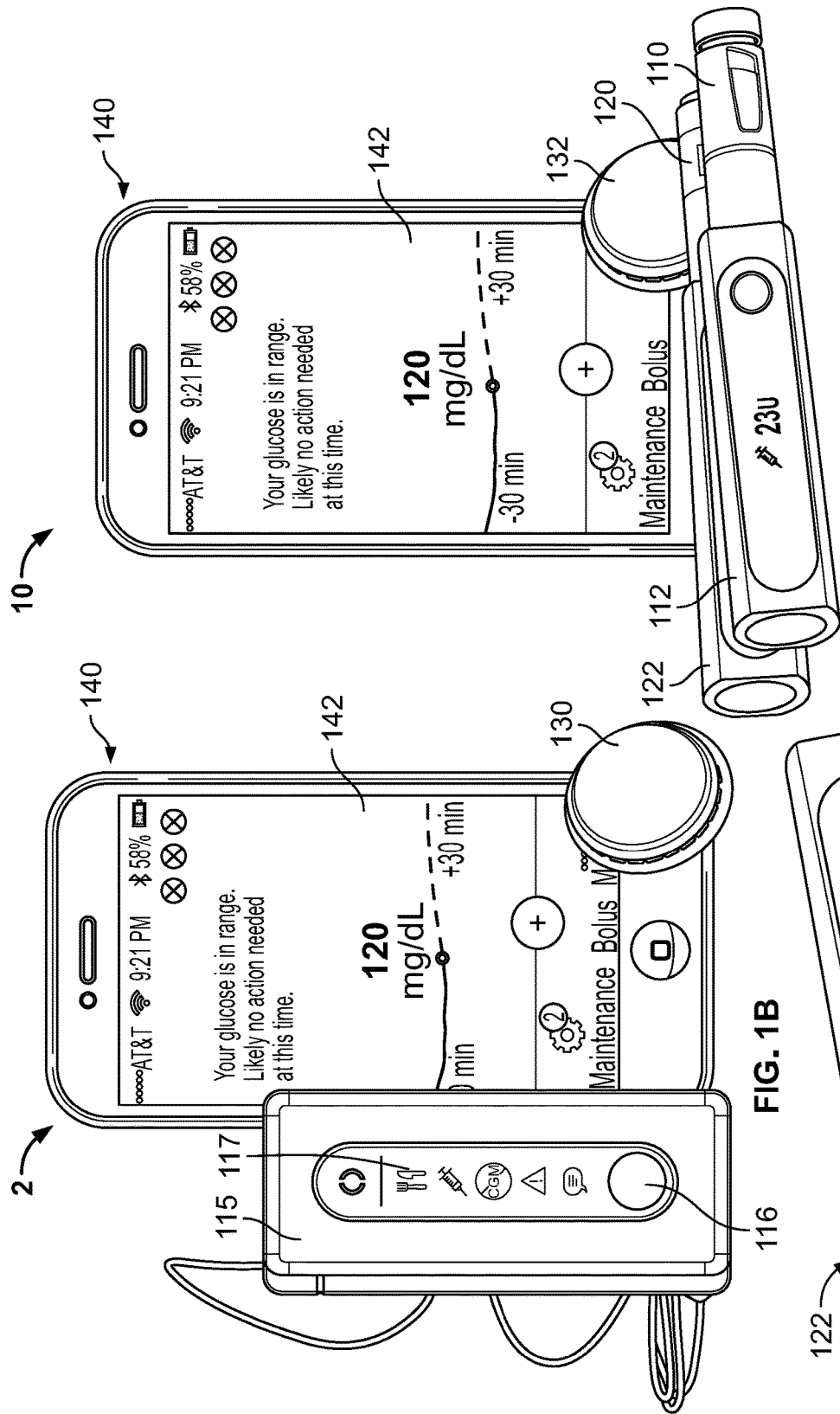
FIG. 1B illustrates an exemplary diabetes management system according to a second embodiment.
FIG. 1C illustrates an exemplary diabetes management system according to a third embodiment.
FIG. 1D illustrates an exemplary pen cap for a medicine injection pen.

FIG. 1B depicts a diabetes management system 2 according to a second embodiment that includes fewer components than the diabetes management device of FIG. 1A. As shown, a mobile device 140 can be a commercial off-the-shelf mobile device (e.g., a smartphone) and can store and execute a mobile application adapted to receive diabetes management information from insulin pump assembly 115, which can be the same as or different from insulin pump assembly 15 of FIG. 1A. As shown, insulin pump assembly 115 includes a button 116 and a series of icons 117 (which may also be present on the insulin pump assembly 15), which can provide the user with status information and/or allow a user to provide instructions or confirmations directly on the insulin pump assembly 115. Alternatively or additionally, the insulin pump assembly can include additional input buttons and/or a display screen for displaying information to the user and allowing the user to provide instructions or confirmations directly on the insulin pump assembly 115. A continuous glucose monitor 130 (which may have all of the features disclosed for glucose sensor 30) is in wireless communication with the insulin pump assembly 115 and/or mobile device 140. The mobile application can depict a graphical display 142 of blood glucose data from the continuous glucose monitor 130.

FIG. 1C depicts a diabetes management system 10 that includes insulin injection pens 110 & 120, a glucose sensor 132 (e.g., a flash glucose monitor or a continuous glucose monitor), and a mobile device 140. The mobile device 140 can be any suitable computing device such as a smartphone, tablet, PDA, smart watch, set top box, personal computer, or a dedicated insulin delivery controller. The mobile device 140 can store and execute a mobile application that is adapted to display therapy relevant information wirelessly received from the other components of the system. As shown, each insulin injection pen 110 and 120 includes a pen cap 112 and 122, respectively. Each pen cap 112 and 122 includes one or more user interface buttons and a display. In the embodiment shown in FIG. 1C, the insulin pens can be commercially mechanical insulin pens that include any suitable insulin, including long-acting insulins and rapid-acting insulins (sometimes called quick-acting insulins or ultra-fast rapid-acting insulins). Suitable rapid-acting insulins include Humalog™, Novolog™, Apidra™, Fiasp™. Suitable long-acting insulins include Lantus™, Levemir™, Toujeo™, Tresiba™. As shown, insulin injection pen 110 represents an exemplary long-acting insulin pen and insulin injection pen 120 represents an exemplary rapid-acting insulin pen. As shown, pen caps 112 and 122 can have distinct colors, shapes, or other indicia, which can be physical or digital, to assist a person with diabetes (PWD) in distinguishing the long-acting pen cap 112 from rapid-acting pen cap 122. Each of the pen caps 112 and 122 can, for example, include different software for performing different actions that are specific to long-acting and rapid-acting insulin delivery pens, respectively. In alternative embodiments, the pen caps 112 and 122 can take the form of another pen accessory that can be secured to each insulin injection pen. In alternative embodiments, each insulin injection pen 110 and 120 can be a reusable insulin pen that includes a display or audio and/or input devices. The insulin injection pens 110 and 120 and/or caps 112 and 122 can be in wireless communication with the mobile device 140 so that data from the insulin injection pens 110 and 120 and/or caps 112 and 122 can be received by and displayed by the mobile application executing on the mobile device 140. The glucose sensor 132 can be any suitable glucose sensor, such as a blood glucose meter (BGM), a flash glucose sensor, or a continuous glucose sensor (CGM). In some cases, the glucose sensor 132 can wirelessly transmit data when interrogated by a reader device (e.g., using NFC communication, RF communication, or another suitable form of wireless or wired communication). In some cases, the glucose sensor 132 can wirelessly transmit data at predetermined intervals (e.g., using radio frequencies) using any suitable communication standard (e.g., BLE). In some cases, the glucose sensor 132 can transmit glucose data using multiple communication techniques. In some cases, the mobile device 140 and/or one or more of the insulin injection pens 110, 120 or pen caps 112, 122 can include an NFC reader adapted to obtain blood glucose data from the glucose sensor 132 when brought within an interrogation distance of the glucose sensor 132. In some cases, the mobile device 140 and/or one or more of the insulin injection pens 110, 120 or pen caps 112, 122 can wirelessly receive blood glucose data from the glucose sensor 132 that is broadcast at predetermined periods of time (e.g., every minute, every 5 minutes, etc.)

When using exemplary diabetes management system 10, a PWD (or their caregiver) would be responsible for determining when to inject insulin and how much to inject, but system 10 could assist the PWD (or caregiver) in determining an appropriate insulin dose based on current data from the glucose sensor, based on stored therapy parameters, and/or based on data about insulin injections. In some cases, the pen caps 112, 122 (or alternatively the pens themselves) can provide data about when the last insulin injection was made. For example, pen caps 112, 122 can detect a time at which the respective cap 112, 122 has been reapplied to its insulin injection pen 110, 120, which can be assumed to be the time of an injection administered to the PWD. In some cases, pen caps 112, 122 can track remaining insulin in an insulin injection pen and determine an amount of each dose. In alternative embodiments, smart pens or pen accessories can detect the dosages set or administered using other suitable techniques. In some cases, such as shown in FIG. 1D, pen caps 112, 122 (or a smartpen or other pen accessory) can depict a time 125 of the most recent dose, or "last dose" on a display 124 which can assist a user in remembering if they have bolused for a recent meal and help a user avoid an unintentional stacking of boluses. In some cases, such as in situations in which the pen caps 112, 122 are capable of detecting an amount of a dose, the display 124 can additionally display the number of units of the last dose. In some cases, the timing of the last dose can include a time zone obtained from the mobile device 140. In some cases, the display might depict a most recently obtained blood glucose level and the time it was obtained. In some cases, the display might be an electronic ink display. In some cases, the display can include identifying information (e.g., a label such as "Sarah's pen") and/or information about the type of insulin pen that it is attached to (e.g., the brand of insulin, or an indicator of rapid or slow acting insulin). In some cases, a notice icon can appear on pen cap 112, 122 in order to indicate to the user that a more detailed suggestion, tip, alert, or alarm is available for the user to view in the mobile application on the mobile device 140.

Figure 3:
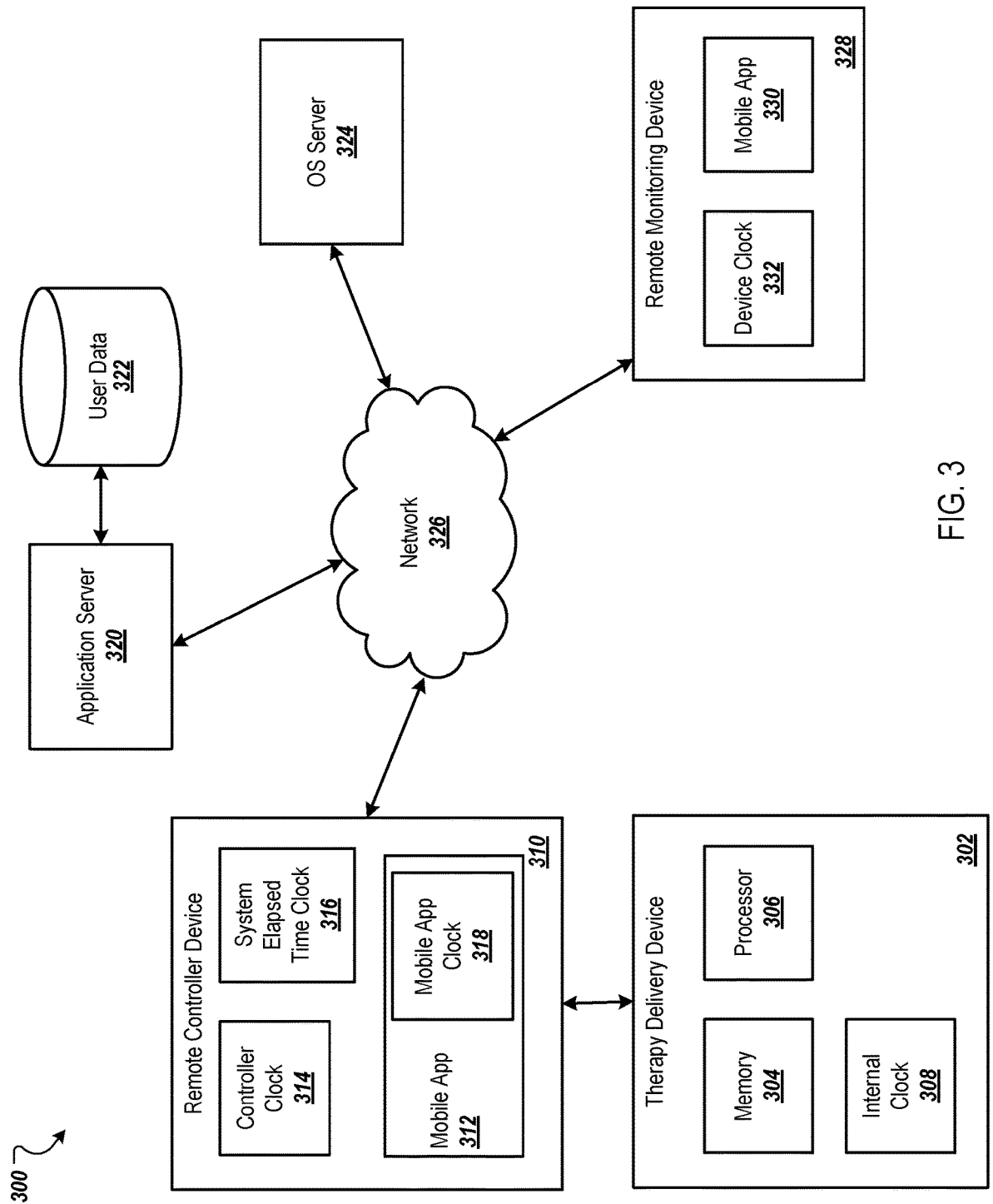
FIG. 3 is a diagram of an example environment in which medical therapy can be administered according to a universal conception of time that is independent of a local time zone and information related to the medical therapy can be presented according to a time zone setting.

FIG. 3 shows a diagram of an example system 300 in which medical therapy can be administered according to a universal conception of time that is independent of a local time zone and information related to the medical therapy can be presented according to a time zone setting. The system 300 includes a therapy delivery device 302 for administering a therapy to a patient, such as, for example, a PWD. The therapy delivery device 302 can be, for example, an insulin delivery device such as the insulin pump assembly 15 of FIG. 1A, the insulin pump assembly 115 of FIG. 1B, or one of the insulin pens 110, 120 in combination with the smart pen caps 112, 122 (respectively) of FIG. 1C. In other embodiments, the therapy delivery device 302 can be a device for administering another type of medication. As yet another example, the therapy delivery device 302 can be a device that assists a user in administering either a medicine or a physical treatment to himself or to a patient. The therapy delivery device 302 includes a memory 304 for storing data related to current and/or past administer therapies, therapies to be administered in the future, medical information related to a patient (e.g., information blood glucose level (BGL)

readings for the patient, such as current BGL, information on meals consumed by the patient, information on recent physical activity by the user, etc.), and other information relevant to administering therapy to the patient. The memory 304 also includes instructions that, when executed by one or more processors 306 of the therapy delivery device 302 cause the therapy delivery device 302 to perform actions such as administering a treatment, determining a treatment amount, communicating with other computing devices, or processing information stored by the memory 304 and/or received from other computing devices or other forms of computer memory.

The therapy delivery device 302 further includes an internal clock 308. The internal clock 308 keeps track of time based on a universal concept of time, such as a Universal Time Coordinated (UTC) clock. The universal concept of time (e.g., the UTC clock) is independent of the current time zone of where the therapy delivery device 302 is located and is also independent of the current time zone or current time zone setting of one or more controlling computing devices (such as remote controller device 310, shown in FIG. 3) in communication with the therapy delivery device 302. For example, the universal concept of time may be Greenwich Mean Time (GMT), Unix Time, or any other time standard that is not dependent on a particular time zone or location of the therapy delivery device 302. The therapy delivery device 302 bases therapy delivery on the universal concept of time maintained by the internal clock 308. The internal clock 308 can be implemented as hardware, software, or a combination of both.

A PWD using the therapy delivery device 302 may require different levels of treatment (e.g., varying basal insulin delivery rates) depending on a time of day. This time based therapy delivery schedule can be, for example, entered by a doctor or other care provider, entered by the PWD (e.g., based on doctor recommendations), or dynamically determined over time based on a pattern of insulin delivery, blood glucose data, and other information. For example, the therapy delivery device 302 can initially include an insulin basal rate delivery schedule that is provided by a doctor for the PWD and gradually update the insulin basal rate delivery schedule overtime based on information received from the PWD, information received from a glucose monitor, and other information received by the therapy delivery device 302. The therapy delivery schedule for the patient can vary, for example, based on times of day when a patient generally eats meals, based on times when the patient is generally awake vs. asleep, based on times when the patient is generally physically active, and/or based on other reoccurring, time-based variables.

The therapy delivery device 302 stores the therapy delivery schedule in memory 304 according to the universal concept of time maintained by the internal clock 308 and administers treatment to the patient based according to the therapy delivery schedule based on time readings of the internal clock 308 provided by the internal clock 308. Alternatively, or in addition to, the therapy delivery schedule, time-of-day specific therapy settings that are used by the therapy delivery device to determine dosages can be stored in the memory 304.

In some implementations, the universal concept of time maintained by the internal clock 308 is initialized on the internal clock 308 at a factory where the therapy delivery device 302 is manufactured. In such scenarios, the internal clock 308 maintains the universal concept of time after it is initially set. In some implementations, the therapy delivery device 302 can include a secondary or backup battery that maintains power to the internal clock 308 when a main battery of the therapy delivery device 302 is being replaced or recharged. In some implementations, the universal concept of time on the internal clock 308 is re-established from a remote server (for example, after a total power loss at the therapy delivery device 302). For example, the therapy delivery device 302 can communicate with a remote server either directly through a network connection or through another computing device, such as the remote controller device 310, that is in communication with a remote server via a network such as the Internet. The remote controller device 310 can be, for example, the smartphones (40, 140, 200) depicted in FIGS. 1A-1C and 2A-2B. The remote server can provide a current time based on the universal concept of time (e.g., Greenwich Mean Time (GMT), Unix Time, or any other time standard that is not dependent on a particular time zone) to the therapy delivery device 302 either directly or indirectly (e.g., via the remote controller device 310) such that the therapy delivery device 302 can re-initialize the internal clock 308. This re-initialization process is described in greater detail below.

Continuing with FIG. 3, the remote controller device 310 is in communication with the therapy delivery device 302. The remote controller device 310 can be a smartphone, a tablet computing device, a wearable computing device, a smartwatch, a fitness tracker, a laptop computer, a desktop computer, a PDA, a dedicated medical therapy system control device, and/or other appropriate computing devices. The remote controller device 310 communicates with the therapy delivery device 302 using near field communication (NFC), RF communication such as 433 RF radio communication, short distance communication (such as BLUETOOTH® based communication), WiFi, or any other suitable wireless or wired communication protocol.

The remote controller device 310 is configured to receive information from the therapy delivery device 302, display information received from the therapy delivery device 302 and from other sources, and provide operating instructions to the therapy delivery device 302 (e.g., such as operating instructions entered by a PWD or a doctor using the remote controller device 310). For example, a mobile application 312 executing on the remote controller device 310 can receive information regarding dispensation of insulin to the PWD and blood glucose levels for the PWD from the therapy delivery device 302 (e.g., BGL information received from a glucose monitor in wireless communication with the therapy delivery device 302 or incorporated as part of the therapy delivery device 302 and then provided to the remote controller device 310 by the therapy delivery device 302). The mobile application 312 executing on the remote controller device 310 can then display the insulin treatment and BGL information via one or more user interface display screens.

In some implementations, the information presented by the mobile application 312 is time-based information, including times that particular basal insulin rates were delivered, times that particular boluses of insulin were delivered, times that BGL measurements were taken, etc. The mobile application 312 can present this time-based information according to a local time zone of the remote controller device 310, a local time zone setting of the remote controller device 310, and/or a manually entered time setting for the remote controller device 310. In the example shown in FIG. 3, the remote controller device 310 includes a controller clock 314 that maintains a time for the remote controller device 310. As discussed with respect to FIGS. 2A-2B, this local time maintained by the controller clock 314 can be automatically determined by the remote controller device 310 based on a location of the remote controller device 310 (e.g., based on a time zone in which the remote controller device 310 is located). For example, the remote controller device 310 can use communications network information (e.g., information on a location of a communications tower or other communications device in communication with the remote controller device 310), GPS information received by a GPS unit of the remote controller device 310, or other location information to determine a location of the remote controller device 310. The remote controller device 310 can then use this location information to determine a time zone for the remote controller device 310. The remote controller device 310 can then automatically set a time for the controller clock 314 based on the time zone where the remote controller device 310 is located. In some instances, this setting of the controller clock 314 based on the time zone of the remote controller device 310 includes receiving time information from a remote server.

Furthermore, as also discussed with respect to FIGS. 2A-2B, the local time maintained by the controller clock 314 can be automatically determined by the remote controller device 310 based on a manually entered time zone setting. For example, as previously discussed, the user of the remote controller device 310 can manually enter a time zone for the remote controller device 310 (that may or may not correspond to a physical location of the remote controller device 310) and the remote controller device 310 can set the controller clock 314 time based on that manually entered time zone. In yet other cases, as discussed with respect to FIGS. 2A-2B, this local time maintained by the controller clock 314 can be based on manual date and time information entered by the user of the remote controller device 310. For example, the user can manually enter a date and time and the controller clock 314 can begin to count time from that manually entered starting time.

As previously discussed, the mobile application 312 can present time-based information (e.g., insulin delivery schedule information, BGL readings, etc.) to the user based on the universal concept of time adjusted by the local time zone. In some implementations, this display of time-based information is displayed in association with one or more times that are independent of a local time maintained by the controller clock 314. In some implementations, the local time maintained by the controller clock 314 can be used to determine times for display along with time-based information. Presenting the time-based information based on the local time maintained by the controller clock 314 can help the user to better process and readily understand the information presented because the user will be able to easily compare the time-based information to a local time of the remote controller device 310 (e.g., as displayed by the remote controller device 310 either inside or separate from the mobile application 312). In some implementations, the time-based information received from the therapy delivery device 302 includes timestamps for the information that are based on the universal concept of time maintained by the internal clock 308 of the therapy delivery device 302. The mobile application 312 (or another application running on the remote controller device 310) then converts the timestamp information from the times based on the universal concept of time to times based on the local time zone of the remote controller device 310 by adjusting the time based on the universal concept of time using the local time zone. The information is then displayed based on the local time maintained by the controller clock 314. In some implementations, the local time maintained by the controller clock 314 can be used to convert the time stamp information from the time based on the universal concept of time to a time for display to a user. In some implementations, the therapy delivery device 302 can query the remote controller device 310 for the local time maintained by the remote controller device 310 and convert the timestamp data for the time-based information from the universal concept of time to times based on the local time maintained by the controller clock 314 of the remote controller device 310 prior to transmitting the time-based information to the remote controller device 310.

In some implementations, the mobile application 312 presents time-based therapy information based on a local time zone of the remote controller device 310 yet independent of a time maintained by the controller clock 314. For example, the user of the remote controller device 310 may manually change time settings or time zone settings for the controller clock 314. The mobile application 312 can display time-based information based on a correct local time for the local time zone in which the remote controller device 310 independent of a manual time setting for the controller clock 314.

In some implementations, the mobile application 312 maintains a system elapsed time clock 316. The system elapsed time clock 316 can be maintained as part of the mobile application 312 or can be separate from the mobile application 312. The system elapsed time clock 316 records a time elapsed since the most recent start/reboot of the mobile application 312. In some implementations, this system elapsed time maintained by the system elapsed time clock 316 is lost each time the mobile application 312 is rebooted.

In some implementations, the mobile application 312 maintains an internal mobile application clock 318. In some implementations, this mobile application clock 318 is lost each time the mobile application 312 is rebooted. The mobile application 312 can use the system elapsed time clock 316 and time information received from a remote server (e.g., an application server 320 associated with the mobile application 312, an operating system server 324 associated with the operating system of the remote controller device 310, or another remote server) through a network 326 (e.g., the Internet) or time information received from the therapy delivery device 302 (e.g., the universal concept of time maintained by the internal clock 308 of the therapy delivery device 302).

For example, the mobile application 312 can communicate with the application server 320 that is associated with the mobile application 312 via the network 326. Upon reboot, the mobile application clock 318 of the mobile application 312 is not initialized. The mobile application 312 can use time information received from the application server 320 to initialize a time for the mobile application clock 318. In this way, the mobile application clock 318 can be initialized independently of the controller clock 314 (which, as previously discussed, may or may not be reflective of an accurate time for the correct time zone for the remote controller device 310. In some implementations, the time information received by the mobile application 312 from the application server 320 is a based on a universal concept of time, such as a Universal Time Coordinated (UTC) clock, maintained by a therapy deliver device. The universal concept of time (e.g., the UTC clock) is independent of the current time zone of where the use is or where any component of the system is located. For example, the universal concept of time may be Greenwich Mean Time (GMT), Unix Time, or any other time standard that is not dependent on a particular time zone. The mobile application 312 can then set the mobile application clock 318 to maintain the universal concept of time. Alternatively, the mobile application 312 can determine a current local time for the remote controller device 310 based on the received time information indicating the time based on the universal concept of time and a local time zone for the remote controller device 310. For example, the local time zone for the remote controller device 310 can be used by the mobile application 312 to determine a time offset to add or subtract to/from the received time based on the universal concept of time and this adjusted time can be used to initialize the mobile application clock 318. In some implementations, this process of initializing the mobile application clock 318 is performed each time the mobile application 312 is started. In some implementations, the time information based on the universal concept of time is received from a server other than the application server 320, such as the operating system server 324 or a dedicated time server.

In some instances, the mobile application 312 may not be able to receive time information from the application server 320 (or another remote server). For example, the remote controller device 310 may be out of communications range from a wireless communications access point, such as a WiFi router or cell phone tower. As another example, the user of the remote controller device 310 may disable wireless and/or wired communications for the remote controller device 310 (e.g., by placing the remote controller device 310 in an "airplane mode" or by disabling WiFi, NFC, RF or other communications functionality). In such instances, upon startup, the mobile application 312 can be configured to initialize the mobile application clock 318 based on timestamped information received from the therapy delivery device 302.

As previously described, the therapy delivery device 302 maintains a universal concept of time using the internal clock 308 independently of times maintained by the remote controller device 310 (such as the controller clock 314). The mobile application 312 receives timestamped information from the therapy delivery device 302 (e.g., timestamped insulin delivery information and BGL information). The mobile application 312 marks the received information with an additional timestamp based on the system elapsed time maintained by the system elapsed time clock 316 to indicate an amount of time elapsed between the most recent startup of the mobile application 312 and the time that the particular timestamped information was received. The mobile application 312 can then use this information to initialize the mobile application clock 318 by determining a current system elapsed time based on the system elapsed time clock 316, comparing the current system elapsed time to the system elapsed timestamp associated with the timestamped treatment information from the therapy delivery device 302 to determine a time elapsed since the timestamped treatment information was received from the therapy delivery device 302. This calculated elapsed time is then added to the timestamp based on the universal concept of time that is associated with the timestamped treatment information to determine a current time based on the universal concept of time. The mobile application 312 then sets the mobile application clock 318 based on this calculated current time based on the universal concept of time. In some implementations, setting the mobile application clock 318 based on the calculated current time based on the universal concept of time includes adding or subtracting a time zone based offset to/from the calculated current time based on the universal concept of time to determine a current time based on a local time zone of the remote controller device 310 and then initializing the mobile application clock 318 based on this calculated current time based on the local time zone.

After initializing the mobile application clock 318, the mobile application 312 can present time-based information to the user based on the time maintained by the mobile application clock 318. The mobile application 312 presents the time-based information based on a current time based on the current time zone location of the remote controller device 310 that is independent of the time zone setting for the time maintained by the controller clock 314.

In some implementations, the mobile application 312 provides time-based information (e.g., insulin delivery information and BGL information) to the application server 320. This time-based information is provided with timestamps based on the universal concept of time. The application server 320 can then store the time-based information in a user database 322. The application server 320 can also access the user database 322 to retrieve information for a PWD associated with the therapy delivery device 302 and provide the information to the remote controller device 310 for presentation within the mobile application 312. Additionally, the application server 320 can access the user database 322 to retrieve treatment information that can be provided to the remote controller device 310 to allow the controller clock 314 to adjust treatment parameters (e.g., adjust an insulin delivery rate schedule) for the PWD.

In some implementations, the system 300 further includes a remote monitoring device 328. In some cases, system 300 can include multiple remote monitoring devices 328. The remote monitoring device 328 can be, for example, a smartphone, a tablet computing device, a wearable computing device, a smartwatch, a fitness tracker, a laptop computer, a desktop computer, a PDA, a dedicated medical therapy system monitoring device, and/or other appropriate computing devices. A person associated with the PWD can use the remote monitoring device 328 to monitor BGL readings and insulin delivery therapy for the PWD. For example, the remote monitoring device 328 can be a tablet in possession of a doctor for the PWD that can allow the doctor to view time-based treatment information and BGL information for the PWD. As another example, the remote monitoring device 328 can be a smartphone of a parent of the PWD (e.g., because the PWD is a minor) that allows the parent to monitor the PWD's treatments and BGLs.

The remote monitoring device 328 can include a mobile application 330 that presents time-based therapy information to the user of the remote monitoring device 328. The mobile application 330 can be, for example, another instance of the mobile application 312 executing on the remote monitoring device 328. The remote monitoring device 328 can also include a device clock 332 that maintains a local time for the remote monitoring device 328. The device clock 332 can be, for example, similar to the controller clock 314 or similar to the mobile application clock 318. The mobile application 330 can be configured to present time-based information based on a local time as indicated by the device clock 332, based on a local time for the PWD as maintained by the mobile application clock 318, or based on a local time for the PWD as maintained by the controller clock 314. In some implementations, the remote monitoring device 328 receives information related to treatments for the PWD from the application server 320 via the network 326. In some implementations, the remote monitoring device 328 receives information related to treatments for the PWD directly from the remote controller device 310 via the network 326. In some implementations, a user of the remote monitoring device 328 can adjust settings for the therapy delivery device 302 using the mobile application 330. For example, a doctor for the PWD can use the mobile application 330 to view time-based therapy information and then adjust a basal insulin delivery rate schedule for the PWD. This updated basal insulin delivery rate schedule is provided to the mobile application 312 executing on the remote controller device 310 (either directly through the network 326 or via the application server 320) and the mobile application 312 can then communicate the adjusted basal insulin delivery rate schedule to the therapy delivery device 302 to update treatment for the PWD.

In some implementations, one or more devices within a medical therapy management system, such as the system 300 or the diabetes management system 1, may have an internal clock that drifts from a precise universal concept of time. For example, the internal clock 308 of the therapy delivery device 302, the remote controller device 310, the application server 320, the remote monitoring device 328, or another component of the system 300 may be imperfect and slightly drift from the precise universal concept of time (e.g., as kept by official time keeping authorities). For example, it is possible that in some scenarios, the internal clock 308 of the therapy delivery device 302 or the internal clock of the remote controller device 310 may drift off of the correct time by 5 seconds per week.

In such scenarios, in some implementations, the device, such as the therapy delivery device 302, can periodically correct the time for its internal clock 308. For example, the therapy delivery device 302 can communicate with the remote controller device 310, the application server 320, and/or another remote server to receive an accurate indication of the current time (based on either the universal concept of time or on a current time zone of the therapy delivery device 302). The therapy delivery device 302 can then reinitialize its internal clock 308 based on the received accurate indication of the current time.

In some implementations, the device that is correcting its internal clock 308 will ensure that it is safe to adjust the clock by identifying a safe clock adjustment period. Identifying a safe clock adjustment period can ensure that accurate dosages are proved to the PWD and that accurate BGL and other measurements are taken. For example, identifying a safe clock adjustment period can prevent under dosage from a bolus dosage being unintentionally skipped or cut short and can also prevent over dosage from a bolus dosage being unintentionally administered twice or for longer than calculated.

A safe clock adjustment period can be defined as a time during which the diabetes management system is not administering a bolus dosage or currently taking a BGL reading. As another example, the safe clock adjustment period can be defined as time when a bolus dosage has not been administered or is not to be administered and a BGL reading has not been taken or is not to be taken within a specified time window, in both the past and future. The specified time window can be selected to be, for example, greater than an expected or maximum time correction period. For example, if the internal clock 308 of the therapy delivery device 302 drifts by approximately 5 seconds per week, and the time correction occurs approximately once per week, the specified time window can be selected as 10 or 15 seconds such that it is sufficiently greater than the predicted drift for the internal clock. In some implementations, the safe clock adjustment period can be defined as a time during which neither a bolus dosage or basal dosage change is occurring and when a glucose reading is not being taken. In some implementations, the safe clock adjustment period can be defined as time when a bolus dosage has not been administered or is not to be administered, a basal dosage has not been administered (or changed) or is not to be administered (or changed), and a BGL reading has not been taken or is not to be taken within a specified time window, in both the past and future.

For example, the therapy delivery device 302 can be programmed to correct its internal clock 308 to correct for drift approximately once per day. Upon expiration of a clock adjustment timer (e.g., a 24 hour timer, or a 23 hour and 58 minute timer), the therapy delivery device 302 can check for a safe clock adjustment period. The therapy delivery device 302 can check for a safe clock adjustment period by periodically (e.g., every 2 seconds) checking for a period in time in which a bolus dosage, a basal dosage rate change, or a BGL reading has not been taken within the specified time window and there is no scheduled bolus dosage, basal dosage rate change, or BGL reading within the specified time window. Upon identifying such a point in time, the therapy delivery device 302 can perform a clock correction action to adjust the internal clock 308 of the therapy delivery device 302. For example, the therapy delivery device 302 can request a time based on the universal concept of time from the remote controller device 310 which can in turn request a current time based on the universal concept of time from the application server 320 or from another remote device having an accurate/trusted clock. The remote controller device 310 then provides the accurate time to the therapy delivery device 302 such that the therapy delivery device 302 can correct the internal clock 308 to correct for time drift of the internal clock 308. In some implementations, the therapy delivery device 302 can periodically identify safe times to adjust the time of the internal clock 308. In some implementations, clock firmware can set a flag to inform software running on the therapy delivery device 302 to inform the clock firmware when there is a safe time to adjust the internal clock 308.

FIGS. 4A and 4B show exemplary user interfaces for viewing medical therapy related information related to medical therapy administered by a time-dependent therapy management system, such as the system 300 of FIG. 3, the system 1 of FIG. 1A, the system 2 of FIG. 1B, and the system 10 of FIG. 1C. The displayed user interfaces can also be used to adjust the time-dependent therapy management system. Turning to FIG. 4A, mobile device 400 can execute an exemplary user interface 410. For example, the mobile device 400 can be the remote controller device 310 of FIG. 3 and the user interface 410 can be a user interface of the mobile application 312. As another example, the mobile device 400 can be the remote monitoring device 328 of FIG. 3 and the user interface 410 can be a user interface of the mobile application 330. The mobile device 400 can also be the mobile device 40 of FIG. 1A or the mobile device 140 of FIGS. 1B and 1C. As described above, the mobile device 400 can be in communication with a therapy delivery device and a remote application server.

The user interface 410 can display information related to treatment administered to or to be administered to a PWD. The user interface 410 can include a message 420 that provides a summary of information displayed in a graphical nature elsewhere by the user interface 410, provides alerts to the user, or otherwise updates the user on relevant information. For example, the message 420 can indicate a current or past BGL trend for the PWD. As another example, the message 420 can remind the PWD to administer a bolus of insulin. As yet another example, the message 420 can suggest that the PWD consume food based on recent BGL readings. The user interface includes a BGL trend line 430 that includes an indication of a current BGL 431, a past BGL trend 432 representative of past BGL readings, and a future predicted BGL trend 433 over a future time frame. The future predicted BGL trend 433 can be based on past and current BGL readings, insulin delivery information (both basal and bolus), food consumption information, insulin sensitivity information for the PWD, and/or other collected or stored information. The user interface 410 can also provide a numerical indicator of a current BGL for the PWD. In some implementations, the BGL trend line 430 is presented along with time information to indicate times of the past collected BGL information, the current BGL information, and the predicted future BGLs. This time information can be based, for example, on a local time maintained by a mobile application clock (such as the mobile application clock 318) that is independent of a system clock for the mobile device 400.

The user interface 410 can additionally include other user interface icons 440 that can be selected by the user (e.g., using touchscreen functionality of the mobile device 400) to add a blood glucose measurement (e.g., a manually taken BGL reading), prompt a suggested bolus calculation, or to change settings of the associated therapy delivery device.

Turning to FIG. 4B, a second screen of the user interface 410 on the mobile device 400 shows additional time-based information related to treatments for the PWD. For example, the user interface 410 includes a graph 450 of collected BGL readings for the user over time, a graph 460 of basal insulin delivery for the PWD over time, and an indication of the most recently administered bolus insulin delivery 470 that includes an amount of the bolus and a time of the bolus. In some implementations, this time-based information is presented using time indicators reflecting times based on a local time zone of the mobile device 400 that is based on a mobile application clock, such as the mobile application clock 318 of FIG. 3. This mobile application clock can be maintained independently of a system clock for the mobile device 400, as described above with respect to FIG. 3. In some implementations, for example where the mobile device 400 is a remote monitoring device such as the remote monitoring device 328, the time information is presented based on a local time zone of the therapy delivery device, which may be in a different time zone than the mobile device 400. In some implementations, the user interface 410 includes an indication of the time zone used as a basis for the times displayed along with the time-based information. In some implementations, the user interface 410 includes an indication of the current time as maintained by the mobile application clock (e.g., the mobile application clock 318).

The user interface 410 can further include status information 480 for a medication pump of the time-dependent therapy management system. For example, the pump status information 480 can indicate an amount of insulin remaining in the pump and an amount of time that has elapsed since all or a portion of the pump body has been replaced (e.g. since a disposable portion of the pump has been replaced, or since a new medication cartridge has been inserted into the pump).

In some cases, a PWD will often travel between locations in different time zones. As such, in some implementations, the user interface 410 can utilize information on the universal concept of time and the current time zone of the mobile device 400 to display time related treatment information to the PWD based on the current (new) time zone of the mobile device 400. Such functionality is especially useful when a PWD wishes to view historic information on previously administered bolus dosages, basal rates, blood glucose readings, or other information that was recorded when the PWD (and the mobile device 400) was located in a time zone that differs from the current time zone in which the PWD located at the time of viewing the historic information.

For example, a PWD can utilize diabetes management system, such as the diabetes management system 1 of FIG. 1A, to administer a bolus dosage of insulin in Milpitas, Calif., which is located in the Pacific Time Zone of the United States, at 7:00 am local time. The mobile device 400 can log the administration of the bolus dosage by recording the amount of bolus dosage along with a time stamp for the bolus dosage based on the universal concept of time (rather than a time stamp based on the local time of the mobile computing device 400) in memory of the mobile device 400. Alternatively, or in addition, the bolus dosage can be logged by storing the bolus dosage amount and the corresponding time stamp based on the universal concept of time at a remote location, such as the user database 322 of FIG. 3, memory of the remote monitoring device 328 of FIG. 3, or memory 304 of the therapy delivery device 302 of FIG. 3. In some implementations, when logging the bolus dosage amount and time stamp, information indicating the time zone in which the bolus dosage occurred is also recorded at the mobile device 400 (or remote location). Other information regarding the PWD's use of the diabetes management system, such as basal dosage rates, BGL readings, etc., is also recorded by the mobile device 400 (or at the remote location) along with time stamp information based on the universal concept of time and, in some implementations, an indication of the time zone in which the mobile device 400 was located when the particular reading was recorded.

Continuing with this example, after administering the bolus dosage in Milpitas, Calif., the PWD travels to Gainesville, Fla., which is located in the Eastern Time Zone of the United States (three hours ahead of the Pacific Time Zone). In some implementations, the mobile device 400, another component of the diabetes management system, or a remote computing device, such as user database 322, can record that the PWD has entered a new time zone and record both the new and previous time zones for the PWD. The PWD then accesses the user interface on the mobile device 400 to review historic treatment information, including the bolus dosage administered at 7:00 am, local time, in Milpitas, Calif. The mobile device 400 accesses the logged information for the bolus dosage (or contacts a remote computing device to retrieve the relevant information). The mobile device 400 can also detect the current time zone for the mobile device 400 and convert the time stamp associated with the bolus dosage information from the universal concept of time to a time based on the current time zone for the mobile device 400. In this example, because the mobile device 400 is now located in the Eastern Time Zone, the mobile device 400 interprets the bolus dosage (which was administered at 7:00 am in the Pacific Time Zone) as having occurred at 10:00 am in the mobile device 400's current time zone (the Eastern Time Zone). The mobile device 400 can then cause the user interface 410 to display an indication that the bolus dosage occurred at 10:00 am. For example, the user interface 410 can display the bolus dosage along with other bolus dosages in a graph or textual representation along with times of administration for each bolus dosage displayed based on the current time zone of the mobile device 400.

The user interface 410 can display other time based information based on the current time zone of the mobile device 400, regardless of the time zone in which the mobile device 400 was located when the information was recorded because the time stamps for the information are recorded based on the universal concept of time rather than the time zone in which the mobile device 400 was located when the information was recorded. For example, after arriving in Gainesville, the PWD can view the graph 450 of collected BGL readings or the graph 460 of basal insulin delivery. The user interface 410 can display the graphs 450 and 460 over a time axis that is based on the current time zone of the mobile device 400. Therefore, a BGL reading that was recorded at 5:00 am local time when the PWD was located in Milpitas is displayed as having occurred at 8:00 am when the PWD views the information while located in Gainesville.

In some implementations, when the PWD travels between time zones, the mobile device 400 will calculate two times off of a single time stamp based on the universal concept of time, one time based on the current time zone of the mobile device 400 and one based on the time zone in which the mobile device 400 was located when the information was logged. Continuing with the above example, the mobile device 400 can, using the time stamp based on the universal concept of time, calculate a time at which the bolus dosage was administered in the Pacific Time Zone and a time at which the bolus dosage was administered in the Eastern Time Zone. The mobile device 400 then causes the user interface 410 to display the bolus dosage along with information indicating both the time based on the current time zone and based on the time zone when the information was recorded. The user interface 410 can also include an indication of the location or time zone of the particular information. For example, for the bolus dosage administered at 7:00 am, local time, in Milpitas, when the PWD later views the information on this bolus dosage in Gainesville, the user interface 410 can include an indication that the bolus dosage was administered at 10:00 am with a parenthetical indicating that the bolus dosage was administered at 7:00 Pacific Time (e.g., by reading "(7:00 am Pacific Time)"; "(7:00 am in Milpitas, Calif.)"; or "(7:00 am Pacific Time in Milpitas, Calif.)").

As another example, the graph 450 of collected BGL readings and/or the graph 460 of basal insulin delivery can be displayed with a first time axis based on the current time zone of the mobile device 400 at the time of viewing along with a second time axis displayed below or near the first time axis that indicates the times based on the time zone in which the mobile device 400 was located when the readings were recorded along with an indication of the location and/or time zone of the mobile device 400 at the time of the readings. In some cases, the second time axis is visually distinguished from the first time axis by being displayed in a different color, in a smaller font, or by being partially grayed out.

By displaying historic time based treatment information using both times based on the current time zone of the mobile device 400 and the time zone in which the mobile device 400 at the times the data points were recorded, the user interface 410 can provide a level of confidence to the PWD that the information was properly recorded and that the PWDs treatment schedule has not been disrupted due to the change in time zone. By recording the time based information using time stamps based on the universal concept of time, the diabetes management system can ensure that the PWD continues to receive proper insulin dosages. Recording the time based information based on the universal concept of time is particularly important when the PWD travels to time zones that are earlier than the time zone in which the reading was recorded. For example, if a bolus dosage taken in Florida is not time zone corrected when viewed in California, it may appear to the user that the dosage was taken in the future as compared to the current time in California, which could lead to irregular and potentially dangerous outcomes.

Figure 5A:
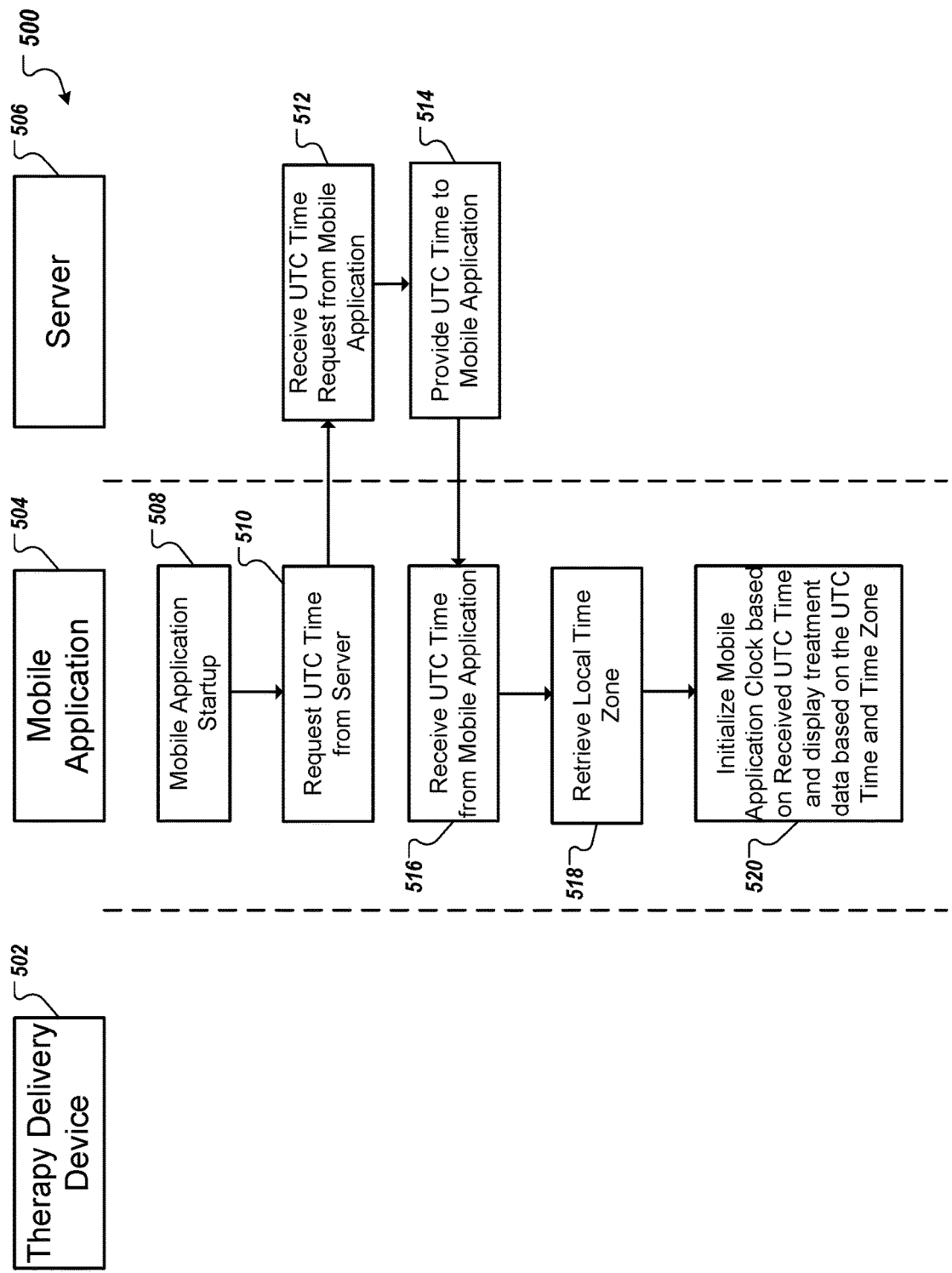
FIG. 5A is a swim-lane flow chart diagram showing actions performed by and communications between various devices of a time-dependent therapy management system during a first time initialization process.

FIG. 5A shows a swim-lane flow chart diagram of a process 500 performed by and communications between various devices of a time-dependent therapy management system during a first process for re-initializing a time setting for a mobile application 504. The mobile application 504 can be, for example, a mobile application executing on a smartphone, a tablet computing device, a wearable computing device, a smartwatch, a fitness tracker, a laptop computer, a desktop computer, a PDA, a dedicated medical therapy system control device, and/or other appropriate computing devices. The mobile application 504 can be, for example, a mobile application executing on the mobile device 40 of FIG. 1A, the mobile device 140 of FIGS. 1B-1C, or the remote controller device 310 of FIG. 3. The mobile application 504 can be, for example, the mobile application 312 executing on the remote controller device 310 of FIG. 3. The mobile application 504 is in communication with a therapy delivery device 502 such that the mobile application 504 can receive therapy delivery information (e.g., insulin dosage amounts and times), blood glucose level information, or other medical therapy information from the therapy delivery device 502. The mobile application 504 can also provide therapy information to the therapy delivery device 502, such as a basal insulin delivery rate schedule, and can further be used to control actions of the therapy delivery device 502 and change settings of the therapy delivery device 502.

Some or all of the steps of the process 500 can be performed in response to an internal clock of the mobile application 504 being lost. For example, the mobile application 504 may maintain an internal clock, such as the mobile application clock 318 described with respect to FIG. 3. The internal clock of mobile application 504 may be lost each time the mobile application 504 is restarted. In some embodiments, other events may cause the mobile application 504 to lose its internal clock. The process 500 shows a particular set of steps for initializing an internal clock of the mobile application 504 by querying a remote server. As previously described (and further described below) the mobile application 504 can also or alternatively be configured to initialize an internal clock of the mobile application 504 by querying the therapy delivery device 502.

At 508, the mobile application 504 starts up. For example, a user of the mobile device on which the mobile application 504 is executing can select an icon or a menu item to cause the mobile application 504 to launch. An internal clock of the mobile application 504 is not initialized at startup of the mobile application 504.

The mobile application 504 requests a time based on a universal concept of time that is independent of a time zone setting where the mobile device running the mobile application 504 is located or a time zone setting of the mobile device running the mobile application 504 from a server 506 (510). For example, the mobile application can be in wireless communication with a network access point (such as a cell phone tower, WiFi router, etc.) and transmit a request to the server 506 over the Internet. The requested time based on the universal concept of time that is independent of the time zone can be Universal Time Coordinated (UTC) clock time based on Greenwich Mean Time (GMT), Unix Time, or any other time standard that is not dependent on a particular time zone. The server 506 can be, for example, an application server associated with the mobile application 504, such as, for example, the application server 320 of FIG. 3. In some implementations, the server 506 can be a different server, such as an operating system server for the mobile device on which the mobile application 504 is executing, a dedicated time server, or another server.

The server 506 receives the request for the time based on the universal concept of time from the mobile application 504 (512). The server 506 can receive the request, for example, through the Internet.

The server 506 provides the current time based on the universal concept of time (e.g., the UTC time) to the mobile application 504 (514). For example, the server 506 provides the current time based on the universal concept of time to the mobile application 504 via the same network that the request for the current time was received from the mobile application 504 (e.g., the Internet).

The mobile application 504 receives the current time based on the universal concept of time (e.g., the UTC time) from the server 506 (516).

The mobile application 504 also retrieves the local time zone for the mobile device on which the mobile application 504 is executing (518). In some implementations, the mobile application 504 does not rely on a time zone setting of mobile device (which may be inaccurate, as discussed above), but rather identifies a location of the mobile device and uses this determined location to identify the correct time zone for the current physical location of the mobile device. For example, the mobile application 504 can query a GPS unit or GPS software of the mobile device to determine the current location of the mobile device. As another example, the mobile application 504 can communicate with a remote device to determine a relative location of the computing device (e.g., based on the location of a communications access point). The mobile application 504 can then use the determined location to determine the local time zone for the mobile computing device. For example, the mobile application 504 can query a server (either the server 506 or another server) to identify the correct time zone that correlates to the current location of the mobile device.

The mobile application 504 initializes the mobile application clock based on the received time based on the universal concept of time (520). For example, the mobile application 504 initializes its internal clock to the current time based on the universal concept of time. Optionally, the mobile application 504 can display treatment data based on the time based on the universal concept of time and on the retrieved local time zone. For example, a time zone based offset can be applied to the UTC time to determine the current time in the time zone where the mobile device is located and this adjusted time is used to display treatment information by the mobile application 504. As described above, the mobile application 504 can use the current time zone information to display therapy information (e.g., time identified drug deliveries and BGLs) based on the local time zone of the mobile device even though such information is associated with time stamps based on a different concept of time (e.g., a universal concept of time that is independent of the current time zone of the mobile device).

Figure 5B:
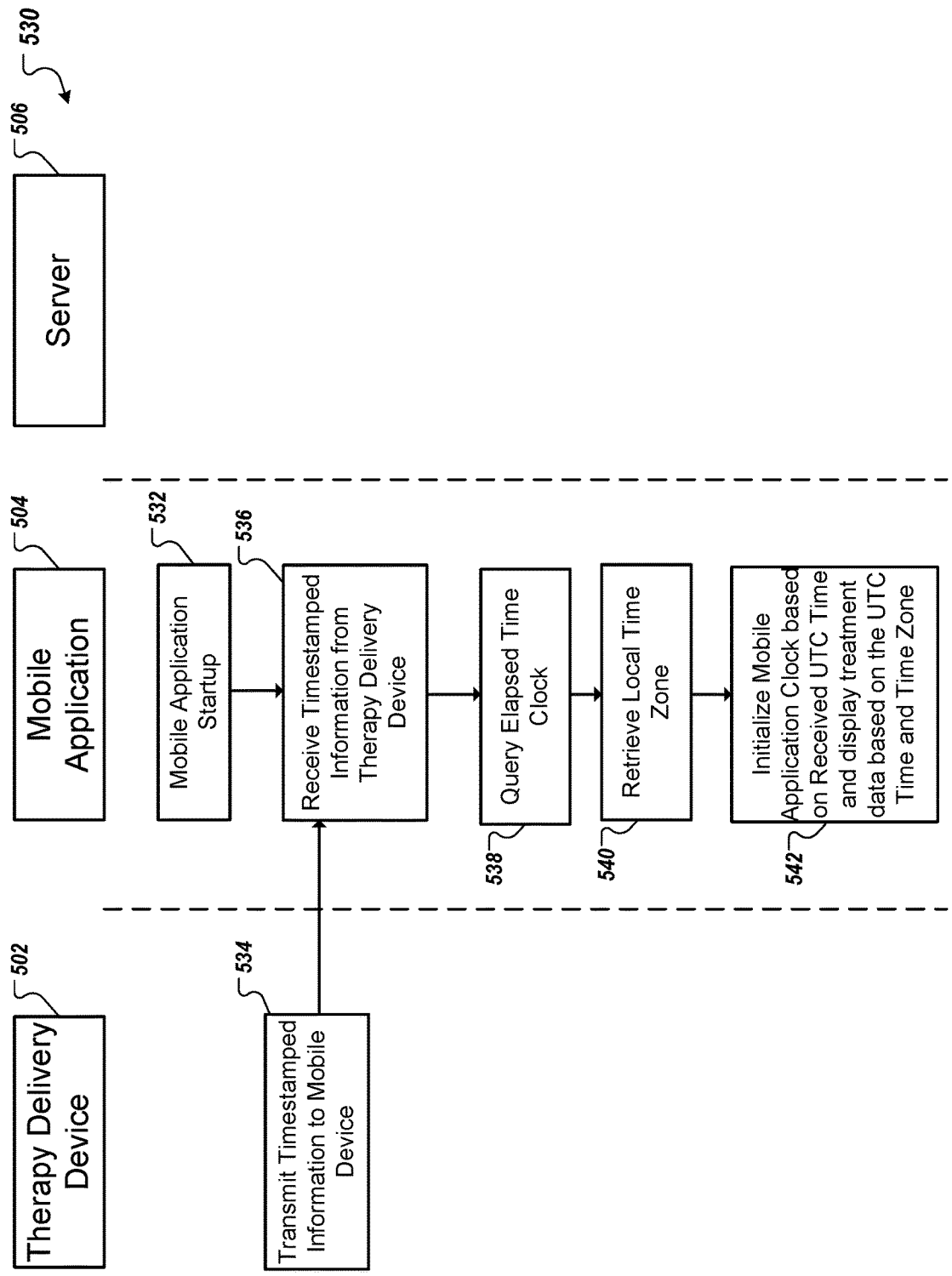
FIG. 5B is a swim-lane flow chart diagram showing actions performed by and communications between various devices of a time-dependent therapy management system during a second time initialization process.

FIG. 5B shows a swim-lane flow chart diagram of an alternative process 530 performed by and communications between various devices of the time-dependent therapy management system of FIG. 5A during a second process for re-initializing a time setting for the mobile application 504. The process 530 relies on time stamped information received from the therapy delivery device 502 rather than querying the server 506 to determine a current time.

At 532, the mobile application 504 starts up. For example, a user of the mobile device on which the mobile application 504 is executing can select an icon or a menu item to cause the mobile application 504 to launch. An internal clock of the mobile application 504 is not initialized at startup of the mobile application 504. The internal clock of mobile application 504 may be lost each time the mobile application 504 is restarted. In some embodiments, other events may cause the mobile application 504 to lose its internal clock.

After the mobile application 504 has started, the therapy delivery device 502 transmits timestamped information to the mobile application 504 (534). For example, the therapy delivery device 502 can communicate with the mobile device on which the mobile application 504 is executing using NFC, RF communications, WiFi, or other suitable communications protocols as previously described. The timestamped information can include, for example, information on delivered basal or bolus insulin deliveries (such as time and amount of insulin delivered), BGL readings, or other information related to treatment of the patient. The timestamps for the timestamped information can be based on a universal concept of time that is independent of a current time zone in which the therapy delivery device 502 and/or the mobile device are located.

The mobile application 504 receives the timestamped information from the therapy delivery device 502 (536). At the time that the timestamped information is received, the mobile application 504 can add an additional timestamp to the received information that indicates how much time elapsed between the most recent startup of the mobile application 504 (e.g., at 532) and the time that the timestamped information is received (at 536). This additional timestamp can come from an elapsed time clock of the mobile device on which the mobile application 504 is executing or an elapsed time clock maintained by the mobile application 504.

The mobile application 504 can initialize an internal clock of the mobile application 504 by querying the elapsed time clock to identify the amount of time that has elapsed between the most recent startup of the mobile application 504 (e.g., at 532) and the current time (538). The mobile application 504 can then identify the difference between the additional timestamp for the received timestamped information (i.e., that identifies the elapsed time identified by the elapsed time clock at the time that the timestamped information was received) and add this difference to the timestamp based on the universal concept of time associated with the timestamped information. This allows the mobile application 504 to identify the current time based on the universal concept of time.

The mobile application 504 also retrieves the local time zone for the mobile device on which the mobile application 504 is executing (540). In some implementations, the mobile application 504 does not rely on a time zone setting of mobile device (which may be inaccurate, as discussed above), but rather identifies a location of the mobile device and uses this determined location to identify the correct time zone for the current physical location of the mobile device. For example, the mobile application 504 can query a GPS unit or GPS software of the mobile device to determine the current location of the mobile device. As another example, the mobile application 504 can communicate with a remote device to determine a relative location of the computing device (e.g., based on the location of a communications access point). The mobile application 504 can then use the determined location to determine the local time zone for the mobile computing device. For example, the mobile application 504 can query a server (either the server 506 or another server) to identify the correct time zone that correlates to the current location of the mobile device.

The mobile application 504 initializes the mobile application clock based on the received time based on the universal concept of time (542). For example, the mobile application 504 initializes its internal clock to the current time based on the universal concept of time. Optionally, the mobile application 504 can display treatment data based on the time based on the universal concept of time and on the retrieved local time zone. For example, a time zone based offset can be applied to the UTC time to determine the current time in the time zone where the mobile device is located and this adjusted time is used to display treatment information by the mobile application 504. As described above, the mobile application 504 can use the current time zone information to display therapy information (e.g., time identified drug deliveries and BGLs) based on the local time zone of the mobile device even such information is associated with time stamps based on a different concept of time (e.g., a universal concept of time that is independent of the current time zone of the mobile device).

Figure 5C:
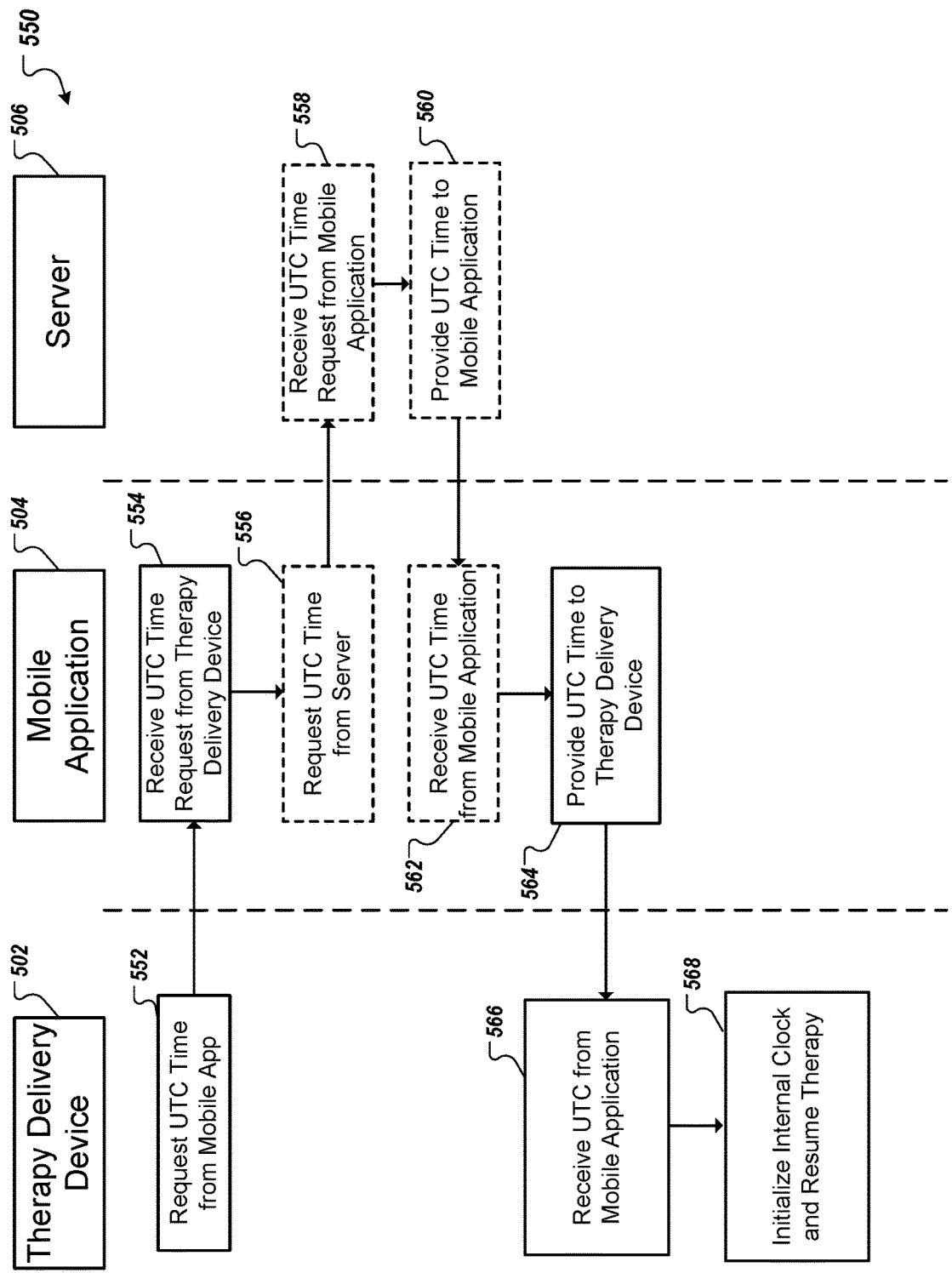
FIG. 5C is a swim-lane flow chart diagram showing actions performed by and communications between various devices of a time-dependent therapy management system during a third time initialization process.

FIG. 5C shows a swim-lane flow chart diagram of a process 550 performed by and communications between various devices of the time-dependent therapy management system of FIG. 5A during a process for re-initializing a time setting for the therapy delivery device 502. For example, the therapy delivery device 502 may lose an internal clock due to total power loss at the therapy delivery device 502 (e.g., both primary and backup batteries have completely exhausted). The therapy delivery device 502 can reinitialize the internal clock by querying the mobile application 504 executing on the mobile device.

At 552, the therapy delivery device 502 requests a current time based on a universal concept of time (e.g., UTC time) from the mobile application 504. For example, the therapy delivery device 502 can communicate with the mobile device on which the mobile application 504 is executing using NFC, RF communications, WiFi, or other suitable communications protocols as previously described.

The mobile application 504 receives the request for the current time based on a universal concept of time (e.g., UTC time) from the therapy delivery device 502 (554). Upon receiving the request, the mobile application 504 can determine if it can provide the UTC time to the therapy delivery device 502 or if the mobile application 504 needs to retrieve the UTC time from another source, such as the server 506. For example, in situations in which the mobile application 504 has been restarted (and therefore has an un-initialized internal clock) and the therapy delivery device 502 has also lost its internal clock (e.g., due to total power loss) prior to the mobile application 504 being able to initialize its internal mobile application clock. In situations in which the internal mobile application clock of the mobile application 504 is not initialized, the process 550 proceeds to optional step 556.

The mobile application 504 requests a time based on a universal concept of time that is independent of a time zone setting where the mobile device running the mobile application 504 is located or a time zone setting of the mobile device running the mobile application 504 from a server 506 (556). For example, the mobile application can be in wireless communication with a network access point (such as a cell phone tower, WiFi router, etc.) and transmit a request to the server 506 over the Internet. The requested time based on the universal concept of time that is independent of the time zone can be Universal Time Coordinated (UTC) clock time based on Greenwich Mean Time (GMT), Unix Time, or any other time standard that is not dependent on a particular time zone. The server 506 can be, for example, an application server associated with the mobile application 504, such as, for example, the application server 320 of FIG. 3. In some implementations, the server 506 can be a different server, such as an operating system server for the mobile device on which the mobile application 504 is executing, a dedicated time server, or another server.

Continuing with the situation in which the internal mobile application clock of the mobile application 504 is not initialized at the time of receiving the request for current time based on the universal concept of time from the therapy delivery device 502 (at 554), the server 506 receives the request for the time based on the universal concept of time from the mobile application 504 (558). The server 506 can receive the request, for example, through the Internet.

Continuing with the situation in which the internal mobile application clock of the mobile application 504 is not initialized at the time of receiving the request for current time based on the universal concept of time from the therapy delivery device 502 (at 554), the server 506 provides the current time based on the universal concept of time (e.g., the UTC time) to the mobile application 504 (560). For example, the server 506 provides the current time based on the universal concept of time to the mobile application 504 via the same network that the request for the current time was received from the mobile application 504 (e.g., the Internet).

Continuing with the situation in which the internal mobile application clock of the mobile application 504 is not initialized at the time of receiving the request for current time based on the universal concept of time from the therapy delivery device 502 (at 554), the mobile application 504 receives the current time based on the universal concept of time (e.g., the UTC time) from the server 506 (562). Upon receiving the current time based on the universal concept of time from the server 506, the mobile application 504 can perform a process for initializing the internal mobile application clock based on the current time based on the universal concept of time received from the server 506. For example, the mobile application 504 can perform some or all of the steps of the process 500 to initialize the internal mobile application clock of the mobile application 504.

The mobile application 504 provides the current time based on the universal concept of time (e.g., UTC time) to the therapy delivery device 502. For example, in situations in which the initialized internal mobile application clock of the mobile application 504 is not initialized (and therefore steps 556-562 of the process 550 are performed), the mobile application 504 can provide the current time based on the universal concept of time received from the server 506 to the therapy delivery device 502. As another example, the mobile application 504 can provide a time based on the current time based on the universal concept of time received from the server 506 to the therapy delivery device 502 (e.g., updated to account for communication and processing lag time).

In scenarios in which the internal mobile application clock of the mobile application 504 is initialized at the time that the request for the current time based on the universal concept of time is received from the therapy delivery device 502 (at 554), the process 550 can skip steps 556-562 and proceed from step 554 to step 564. In some such scenarios, the current time based on the universal concept of time provided to the therapy delivery device 502 by the mobile application 504 is determined based on a time indicated by the internal mobile application clock of the mobile application 504. For example, the mobile application 504 can use the time maintained by the internal mobile application clock and the current time zone for the mobile device on which the mobile application 504 is executing to determine the current time based on the universal concept of time that is independent of the current time zone of the mobile device. The mobile application 504 can then provide the determined current time based on the universal concept of time to the therapy delivery device 502. In some implementations, the mobile application 504 can include an internal mobile application clock that maintains the current time based on the universal concept of time and the mobile application 504 can provide the current time indicated by the internal mobile application clock to the therapy delivery device 502 as the UTC time.

The therapy delivery device 502 receives the current time based on the universal concept of time (e.g., UTC time) from the mobile application 504 (566). The therapy delivery device 502 can, for example, receive the current time based on the universal concept of time from the mobile application 504 using the same communication protocol used to transmit the request for the current time based on the universal concept of time to the mobile application 504.

The therapy delivery device 502 initializes the internal clock using the received current time based on the universal concept of time (568). In some implementations, the therapy delivery device 502 can be configured to suspend therapy if the internal clock of the therapy delivery device 502 is uninitialized. In such implementations, therapy is resumed by the therapy delivery device 502 upon re-initialization of the internal clock. In some implementations, the therapy delivery device 502 can maintain a default therapy delivery schedule if the internal clock is lost (e.g., to ensure that at least some insulin delivered to a PWD) and then resume the regularly scheduled therapy delivery once the internal clock is re-initialized at step 568.

In some situations, both the internal clock of the therapy delivery device 502 and the internal mobile application clock of the mobile application 504 may be lost at relatively the same time. For example, the therapy delivery device 502 may lose power and the mobile application 504 clock may not have initialized prior to the power loss by the therapy delivery device 502. Furthermore, in some such scenarios, the mobile application 504 may be unable to contact the server 506. For example, the mobile device on which the mobile application 504 is executing may be out of wireless communications range or may have wireless communication disabled (e.g., "airplane mode"). In some implementations, when the internal mobile application clock cannot be re-initialized based on the current time based on the universal concept of time due to lack of access to the server 506, the mobile application 504 can be configured to initialize the internal mobile application clock based on another clock maintained by the mobile device on which the mobile application 504 is executing. For example, the mobile application 504 can access a clock maintained by the operating system of the mobile device and set the time indicated by the operating system clock as the time for the internal mobile application clock until such a time that the internal mobile application clock can be initialized based on the current time based on the universal concept of time received from the server 506. In some implementations, the mobile application 504 can set a flag to indicate that the time for the internal mobile application clock is based on the operating system clock and may not be accurate and should therefore be re-initialized when the mobile application 504 regains communications connectivity. Upon regaining communications connectivity, the mobile application 504 can perform some or all of the steps of the process 550 or the process 500 (or the process 530) to re-initialize the internal mobile application clock of the mobile application 504.

In some implementations, the mobile application 504 can determine a current time based on the universal concept of time using the current time indicated by the operating system clock and a current time zone setting for the operating system clock. Although this may be less accurate than a current time based on the universal concept of time provided by the server 506, determining such a current time based on the universal concept of time using settings of the operating system clock can provide a rough estimate of the current time that can still be used for providing therapy delivery to the patient by the therapy delivery device 502 according to a therapy delivery schedule. The mobile application 504 can then provide the current time based on the universal concept of time that is determined based on the operating system clock settings to the therapy delivery device 502 to allow the therapy delivery device 502 to continue therapy delivery according to the therapy delivery schedule. In some implementations, the mobile application 504 can also provide an indicator to the therapy delivery device 502 to indicate that the provided current time is based on operating system clock settings and therefore may not be accurate. The mobile application 504 can later provide an updated current time based on the universal concept of time to the therapy delivery device 502 based on a current time based on the universal concept of time received from the server 506 when communications with the server 506 become available.

As discussed above with respect to FIGS. 5A-5C, several different process for re-initializing a time setting for the various devices in the identified devices (e.g., therapy delivery device 502 and mobile application 504) can be employed. In some cases, some or all of the steps of these processes can be performed together or in tandem to re-initialize one or more of the devices. In some implementations, one process for re-initializing one or more of the devices can be identified as a preferred process for re-initializing the time settings. For example, in situations in which the therapy delivery device 502 has an accurate UTC time, the default process can be for the mobile application 504 to re-initialize its time settings based on the UTC time of the therapy delivery device 502 (as shown, for example, in FIG. 5B). In different embodiments, the mobile application 504 can have a setting for indicating a preference for re-initializing the time setting of the mobile application 504 based on UTC time information received from the therapy delivery device 502 or from the server 506 when both options are available.

In some embodiments, the mobile application 504 maintains a UTC based perception of time by having a perception of UTC time from the therapy delivery device 502 and using an elapsed-time clock based on this UTC time received from the therapy delivery device 502 until the next communication between the mobile application 504 and the therapy delivery device 502. Each time the mobile application 504 communicates with the therapy delivery device 502, the mobile application 504 updates the mobile application clock to match the UTC clock on the therapy delivery device 502. Thus the UTC times maintained by the mobile application 504 and the therapy delivery device 502 are periodically synchronized, with the therapy delivery device 502 maintaining the master clock upon which the mobile application 504 clock is updated. In some embodiments the mobile application 504 will only attempt to retrieve the UTC time from the server if the UTC time is unavailable from the therapy delivery device 502.

The features described in this disclosure can be implemented in digital electronic circuitry, or in computer hardware, firmware, software, or in combinations of them. The systems and apparatus described herein can be implemented in a computer program product tangibly embodied in an information carrier, e.g., in a machine-readable storage device, for execution by a programmable processor; and method steps can be performed by one or more programmable processors executing one or more programs of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing context.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer (e.g., desktop, laptop, server, etc.) or other computing device (e.g., smartphone, tablet, PDA, smart watch, set top box, specialized medical device, or another specialized computing device) having a display device such as a CRT (cathode ray tube), LCD (liquid crystal display), plasma, or other display screen for displaying information to the user and a keyboard, a pointing device such as a mouse or a trackball, a touch screen, input buttons, or other input hardware by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, various forms of the flows shown above may be used, with steps re-ordered, added, or removed. Also, although several applications of the payment systems and methods have been described, it should be recognized that numerous other applications are contemplated. Accordingly, other embodiments are within the scope of the following claims.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A medication delivery system comprising:
a medication delivery device adapted to dispense medication, the medication delivery device comprising memory to store a medication delivery schedule or time-dependent dosage parameters based on a universal concept of time that is independent of a time zone in which the medication delivery device is located, the medication delivery device being further adapted to record medication delivery information or user actions, the medication delivery information or user actions being stored along with timestamps based on the universal concept of time;
a remote computing device in communication with the medication delivery device, the remote computing device configured to receive the timestamped medication delivery information or user actions from the medication delivery device, and present a visual display of the medication delivery information or user actions along with times, wherein the displayed times are determined using the timestamps based on the universal concept of time adjusted based on a current time zone setting of the remote computing device, wherein the remote computing device has a switch with at least (i) a first operating mode where the remote computing device automatically sets the current time zone and a current time for the current time zone, and (ii) a second operating mode where a user enters manual time settings of the current time; and
a mobile application clock maintained by a mobile application associated with the medication delivery device, the mobile application executing on the remote computing device and being distinct from an operating system clock of the remote computing device, wherein, in response to the remote computing device being in the second operating mode, the mobile application clock is configured to use the current time zone setting for the remote computing device to determine a current time for the current time zone of the remote computing device independent of the manual time settings of the remote computing device, wherein the mobile application clock is further configured to use the determined current time, and ignore the manual time settings, when the medication delivery system provides therapy delivery or a therapy recommendation.

2. The medication delivery system of claim 1, wherein:
the medication delivery device is further configured to receive blood glucose level information from a blood glucose monitor and store the blood glucose level information along with timestamps based on the universal concept of time that is independent of the time zone in which the medication delivery device is located; and
the remote computing device is further configured to receive the timestamped blood glucose level information from the medication delivery device, and present a visual display of the blood glucose level information along with times based on the universal concept of time at which the blood glucose levels were determined adjusted based on the current time zone setting of the remote computing device.

3. The medication delivery system of claim 2, wherein the remote computing device is configured to display the medication delivery information and the blood glucose level information concurrently.

4. The medication delivery system of claim 1, wherein the remote computing device is configured to convert the timestamps for the timestamped medication delivery information from times based on the universal concept of time to times based on the current time zone setting of the remote computing device using the mobile application clock maintained by the mobile application.

5. The medication delivery system of claim 4, wherein the mobile application clock is further configured to determine the current time for the current time zone of the remote computing device independent of time zone settings of the remote computing device.

6. The medication delivery system of claim 4, wherein the mobile application executing on the remote computing device is configured to initialize the mobile application clock using a time based on the universal concept of time received from a server.

7. The medication delivery system of claim 6, wherein the server is a mobile application server for the mobile application.

8. The medication delivery system of claim 4, wherein the mobile application executing on the remote computing device is configured to initialize the mobile application clock using timestamped information received from the medication delivery device.

9. The medication delivery system of claim 8, wherein the timestamps for the timestamped information received from the medication delivery device are based on the universal concept of time.

10. The medication delivery system of claim 8, wherein the mobile application executing on the remote computing device is configured to maintain the universal concept of time for the mobile application clock by monitoring an elapsed time since the remote computing device was started or an elapsed time since the mobile application was initialized and comparing the elapsed time associated with information from the medication delivery device that indicates the universal concept of time to a current amount of elapsed time.

11. A medication delivery system comprising:
a medication delivery device adapted to dispense medication, the medication delivery device comprising memory to store a medication delivery schedule or time-dependent dosage parameters based on a universal concept of time that is independent of a time zone in which the medication delivery device is located, the medication delivery device being further adapted to record medication delivery information or user actions, the medication delivery information or user actions being stored along with timestamps based on the universal concept of time; and
a remote computing device in communication with the medication delivery device, the remote computing device configured to receive the timestamped medication delivery information or user actions from the medication delivery device, and present a visual display of the medication delivery information or user actions along with times, wherein the displayed times are determined using the timestamps based on the universal concept of time adjusted based on a current time zone setting of the remote computing device;
wherein the medication delivery device comprises a medication delivery pen and a removable cap affixed to cover a needle of the medication delivery pen, and wherein the removable cap is a removable smart cap that includes the memory to store the medication delivery schedule or time-dependent dosage parameters.

12. The medication delivery system of claim 1, wherein the medication delivery device comprises:

a portable pump housing that receives a medication supply for dispensation to a user, the pump housing at least partially containing a pump drive system to dispense medication from the medication supply through a flow path to the user; and a controller that communicates with the pump drive system to dispense the medication to the user based on the stored medication delivery schedule.

13. The medication delivery system of claim 1, wherein the remote computing device is a smartphone configured to wirelessly communicate with the medication delivery device.

14. The medication delivery system of claim 1, wherein the medication delivery device is configured to maintain a delivery device clock that maintains a current time based on the universal concept of time, and wherein the medication delivery device is configured to initialize the delivery device clock using time information received from the remote computing device.

15. The medication delivery system of claim 1, wherein the medication delivery device comprises a medication delivery pen and a removable cap affixed to the medication delivery pen.

16. The medication delivery system of claim 15, wherein the removable cap is a removable smart cap that includes the memory to store the medication delivery schedule or time-dependent dosage parameters.

17. The medication delivery system of claim 1, wherein the medication delivery device is configured to maintain a delivery device clock that maintains a current time based on the universal concept of time, and wherein the medication delivery device is configured to initialize the delivery device clock using time information received from the remote computing device.

18. The medication delivery system of claim 11, wherein the medication delivery device is configured to maintain a delivery device clock that maintains a current time based on the universal concept of time, and wherein the medication delivery device is configured to initialize the delivery device clock using time information received from the remote computing device.

* * * * *